United States Patent
de Brouwer et al.

(10) Patent No.: US 9,771,452 B2
(45) Date of Patent: Sep. 26, 2017

(54) PLASTIC COMPOSITION COMPRISING A POLYCARBONATE MADE FROM LOW SULFUR BISPHENOL A, AND ARTICLES MADE THEREFROM

(71) Applicant: SABIC Global Technologies B.V., Bergen op Zoom (NL)

(72) Inventors: Johannes de Brouwer, Oisterwijk (NL); Christopher Luke Hein, Evansville, IN (US); Thomas L. Evans, Mt. Vernon, IN (US); Hatem Abdallah Belfadhel, Roosendaal (NL); Marcel Vieveen, De Heen (NL); Christian Wold, Halsteren (NL); Eric Brander, Tholen (NL)

(73) Assignee: SABIC GLOBAL TECHNOLOGIES B.V., Bergen Op Zoom (NL)

(*) Notice: Subject to any disclaimer, the term of this patent is extended or adjusted under 35 U.S.C. 154(b) by 0 days.

(21) Appl. No.: 15/250,244

(22) Filed: Aug. 29, 2016

(65) Prior Publication Data
US 2016/0369049 A1 Dec. 22, 2016

Related U.S. Application Data

(62) Division of application No. 13/779,781, filed on Feb. 28, 2013, now abandoned.
(Continued)

(51) Int. Cl.
*C08G 64/30* (2006.01)
*C08K 3/00* (2006.01)
(Continued)

(52) U.S. Cl.
CPC ............ *C08G 64/307* (2013.01); *C07C 29/78* (2013.01); *C07C 37/20* (2013.01); *C07C 37/84* (2013.01);
(Continued)

(58) Field of Classification Search
CPC .. C08G 64/307; C08G 64/045; C08G 3/0033; H01L 33/502; H01L 33/56; H05B 33/12
See application file for complete search history.

(56) References Cited

U.S. PATENT DOCUMENTS

| 489,803 A | 1/1893 | Gillespie et al. |
| 3,049,568 A | 8/1962 | Apel et al. |
| (Continued) | | |

FOREIGN PATENT DOCUMENTS

| CN | 1204664 A | 1/1999 |
| CN | 1279231 A | 1/2001 |
| (Continued) | | |

OTHER PUBLICATIONS

Anderson et al.; "Quantitative Analysis of Commercial Bisphenol A by Paper Chromatography"; Analytical Chemistry; vol. 31, No. 7; 1959; p. 1214-1217.
(Continued)

*Primary Examiner* — Joseph L Williams
(74) *Attorney, Agent, or Firm* — Cantor Colburn LLP

(57) ABSTRACT

In one embodiment, a light emitting device includes a lighting element located in a housing, wherein the housing is formed from a plastic composition including, for example, a polycarbonate formed from reacting, in the presence of a transesterification catalyst, a diaryl carbonate ester and a bisphenol A, wherein the bisphenol A has a sulfur concentration of 1 ppm to 15 ppm, based upon a weight of the bisphenol A; and a conversion material wherein the conversion material includes an inorganic material that converts radiation of a certain wavelength and re-emits of a different wavelength; wherein after the conversion material has been exposed to an excitation source, the conversion material has a luminescence lifetime of less than $10^{-4}$ seconds when the excitation source is removed.

20 Claims, 5 Drawing Sheets

Related U.S. Application Data

(60) Provisional application No. 61/604,960, filed on Feb. 29, 2012.

(51) Int. Cl.

| | | |
|---|---|---|
| *C08K 9/06* | (2006.01) | |
| *C09K 11/02* | (2006.01) | |
| *H05B 33/12* | (2006.01) | |
| *H01L 33/56* | (2010.01) | |
| *C07C 29/78* | (2006.01) | |
| *C07C 37/20* | (2006.01) | |
| *G02B 1/04* | (2006.01) | |
| *C07C 37/84* | (2006.01) | |
| *C07C 37/86* | (2006.01) | |
| *F21V 29/70* | (2015.01) | |
| *C08G 64/04* | (2006.01) | |
| *C09K 11/57* | (2006.01) | |
| *C09K 11/77* | (2006.01) | |
| *F21V 3/04* | (2006.01) | |
| *F21V 9/16* | (2006.01) | |
| *H01L 33/50* | (2010.01) | |
| *F21Y 115/10* | (2016.01) | |

(52) U.S. Cl.
CPC .......... *C07C 37/86* (2013.01); *C08G 64/045* (2013.01); *C08K 3/0033* (2013.01); *C08K 9/06* (2013.01); *C09K 11/02* (2013.01); *C09K 11/574* (2013.01); *C09K 11/77* (2013.01); *C09K 11/7721* (2013.01); *C09K 11/7734* (2013.01); *F21V 3/0436* (2013.01); *F21V 9/16* (2013.01); *F21V 29/70* (2015.01); *G02B 1/04* (2013.01); *H01L 33/502* (2013.01); *H01L 33/56* (2013.01); *H05B 33/12* (2013.01); *C08K 2201/001* (2013.01); *F21Y 2115/10* (2016.08); *H01L 33/501* (2013.01)

(56) References Cited

U.S. PATENT DOCUMENTS

| | | |
|---|---|---|
| 3,394,089 A | 7/1968 | McNutt et al. |
| 3,673,262 A | 6/1972 | Prahl et al. |
| 3,839,247 A | 10/1974 | Bialous et al. |
| 4,045,379 A | 8/1977 | Kwantes et al. |
| 4,052,466 A | 10/1977 | Sun |
| 4,076,686 A | 2/1978 | Calkins |
| 4,191,843 A | 3/1980 | Kwantes et al. |
| 4,294,995 A | 10/1981 | Faler et al. |
| 4,308,404 A | 12/1981 | Kwantes et al. |
| 4,308,405 A | 12/1981 | Kwantes |
| 4,346,247 A | 8/1982 | Faler et al. |
| 4,365,099 A | 12/1982 | Faler et al. |
| 4,391,997 A | 7/1983 | Mendiratta |
| 4,396,728 A | 8/1983 | Faler |
| 4,400,555 A | 8/1983 | Mendiratta |
| 4,423,252 A | 12/1983 | Maki et al. |
| 4,424,283 A | 1/1984 | Faler et al. |
| 4,455,409 A | 6/1984 | Faler et al. |
| 4,478,956 A | 10/1984 | Maki et al. |
| 4,507,509 A | 3/1985 | Mendiratta et al. |
| 4,584,416 A | 4/1986 | Pressman et al. |
| 4,590,303 A | 5/1986 | Mendiratta |
| 4,595,704 A | 6/1986 | Fazio |
| 4,820,740 A | 4/1989 | Li |
| 4,822,923 A | 4/1989 | Li |
| 4,904,710 A | 2/1990 | Nace |
| 4,918,245 A | 4/1990 | Iimuro et al. |
| 5,015,784 A | 5/1991 | Rudolph et al. |
| 5,064,885 A | 11/1991 | Muller et al. |
| 5,087,767 A | 2/1992 | Okamoto et al. |
| 5,212,206 A | 5/1993 | Rudolph et al. |
| 5,233,096 A | 8/1993 | Lundquist |
| 5,284,981 A | 2/1994 | Rudolph et al. |
| 5,288,926 A | 2/1994 | Patrascu et al. |
| 5,302,774 A | 4/1994 | Berg et al. |
| 5,364,895 A | 11/1994 | Stevenson et al. |
| 5,395,857 A | 3/1995 | Berg et al. |
| 5,414,151 A | 5/1995 | Pressman et al. |
| 5,414,152 A | 5/1995 | Cipullo |
| 5,424,006 A | 6/1995 | Murayama et al. |
| 5,438,086 A | 8/1995 | Stevenson et al. |
| 5,455,282 A | 10/1995 | Berg et al. |
| 5,463,140 A | 10/1995 | Wehmeyer et al. |
| 5,470,938 A | 11/1995 | Sakashita et al. |
| 5,475,154 A | 12/1995 | Lundquist et al. |
| 5,589,517 A | 12/1996 | Sugawara et al. |
| 5,606,007 A | 2/1997 | Sakashita et al. |
| 5,631,338 A | 5/1997 | Inoue et al. |
| 5,672,664 A | 9/1997 | DeRudder et al. |
| 5,698,600 A | 12/1997 | Wulff et al. |
| 5,747,632 A | 5/1998 | Adachi et al. |
| 5,780,690 A | 7/1998 | Berg et al. |
| 5,783,733 A | 7/1998 | Kissinger |
| 5,883,218 A | 3/1999 | Gordon et al. |
| 5,914,431 A | 6/1999 | Fennhoff |
| 5,939,494 A | 8/1999 | Wehmeyer et al. |
| 6,066,861 A | 5/2000 | Hohn et al. |
| 6,069,225 A | 5/2000 | Gerace et al. |
| 6,133,190 A | 10/2000 | Wehmeyer et al. |
| 6,174,987 B1 | 1/2001 | Gordon et al. |
| 6,211,417 B1 | 4/2001 | Fengler et al. |
| 6,329,556 B1 | 12/2001 | Sakura et al. |
| 6,373,262 B1 | 4/2002 | Herring et al. |
| 6,414,199 B1 | 7/2002 | Saruwatari |
| 6,429,343 B1 | 8/2002 | Iwahara |
| 6,486,222 B2 | 11/2002 | Kissinger et al. |
| 6,586,637 B2 | 7/2003 | Iwahara |
| 6,613,823 B1 | 9/2003 | Battiste et al. |
| 6,653,513 B1 | 11/2003 | Iwahara |
| 6,653,613 B1 | 11/2003 | Bucourt et al. |
| 6,676,852 B2 | 1/2004 | Brown et al. |
| 6,692,659 B2 | 2/2004 | Brown et al. |
| 6,706,846 B2 | 3/2004 | Brack et al. |
| 6,710,211 B1 | 3/2004 | Heydenreich et al. |
| 6,716,368 B1 | 4/2004 | Schottland et al. |
| 6,727,394 B2 | 4/2004 | Saruwatari |
| 6,730,816 B2 | 5/2004 | Lundquist |
| 6,740,784 B2 | 5/2004 | Iwahara et al. |
| 6,995,294 B2 | 2/2006 | Webb et al. |
| 7,112,702 B2 | 9/2006 | Carvill et al. |
| 7,112,703 B2 | 9/2006 | Neumann et al. |
| 7,129,382 B2 | 10/2006 | Iwahara et al. |
| 7,227,046 B2 | 6/2007 | Commarieu |
| 7,491,837 B2 | 2/2009 | Schlosberg et al. |
| 7,700,696 B2 | 4/2010 | van de Grampel et al. |
| 7,852,428 B2 | 12/2010 | Byoun et al. |
| 7,879,927 B2 | 2/2011 | Vlottes et al. |
| 7,923,586 B2 | 4/2011 | Stahlbush et al. |
| 7,959,827 B2 | 6/2011 | Comanzo et al. |
| 7,964,273 B2 | 6/2011 | Kogure et al. |
| 7,989,531 B2 | 8/2011 | Bersted et al. |
| 8,250,101 B2 | 8/2012 | Fot et al. |
| 8,735,634 B2 | 5/2014 | Hasyagar et al. |
| 9,006,378 B2 | 4/2015 | van Den Bogerd et al. |
| 9,553,244 B2 | 1/2017 | Morizur et al. |
| 2002/0147256 A1 | 10/2002 | Eckel et al. |
| 2003/0180542 A1 | 9/2003 | Pickett et al. |
| 2003/0232957 A1 | 12/2003 | Silvi et al. |
| 2004/0024105 A1 | 2/2004 | Kim et al. |
| 2004/0077820 A1 | 4/2004 | Silva et al. |
| 2004/0116751 A1 | 6/2004 | Carvill et al. |
| 2004/0135504 A1 | 7/2004 | Tamiki et al. |
| 2004/0181100 A1 | 9/2004 | Lundquist |
| 2004/0227465 A1 | 11/2004 | Menkara et al. |
| 2005/0035331 A1 | 2/2005 | Sun |
| 2005/0070615 A1 | 3/2005 | Terajima et al. |
| 2005/0177007 A1 | 8/2005 | Neumann et al. |
| 2005/0215833 A1 | 9/2005 | Neumann et al. |
| 2006/0069292 A1 | 3/2006 | Kumar et al. |
| 2006/0135690 A1 | 6/2006 | Juikar et al. |
| 2006/0247356 A1 | 11/2006 | Agarwal |

(56) References Cited

U.S. PATENT DOCUMENTS

| | | |
|---|---|---|
| 2006/0263547 A1 | 11/2006 | Cojocariu et al. |
| 2007/0004941 A1 | 1/2007 | Blaschke et al. |
| 2007/0139949 A1 | 6/2007 | Tanda et al. |
| 2007/0299169 A1 | 12/2007 | Ohira et al. |
| 2008/0029720 A1 | 2/2008 | Li |
| 2008/0081855 A1 | 4/2008 | Mullen |
| 2008/0113117 A1 | 5/2008 | Coenjarts et al. |
| 2009/0021141 A1 | 1/2009 | Emoto et al. |
| 2009/0043053 A1 | 2/2009 | Gorny et al. |
| 2009/0054586 A1 | 2/2009 | Hein et al. |
| 2010/0006875 A1 | 1/2010 | Naum et al. |
| 2010/0137549 A1 | 6/2010 | Takahashi et al. |
| 2010/0155758 A1 | 6/2010 | Kumei et al. |
| 2010/0164367 A1 | 7/2010 | Shioi et al. |
| 2010/0200874 A1 | 8/2010 | Shioi et al. |
| 2010/0261828 A1 | 10/2010 | Tomoda et al. |
| 2011/0127904 A1 | 6/2011 | Tsai |
| 2011/0140593 A1 | 6/2011 | Negley et al. |
| 2011/0151262 A1 | 6/2011 | Heuer et al. |
| 2011/0278614 A1 | 11/2011 | Maier-Richter et al. |
| 2012/0043552 A1 | 2/2012 | David et al. |
| 2012/0119234 A1 | 5/2012 | Shioi et al. |
| 2012/0181482 A1 | 7/2012 | Xiao et al. |
| 2012/0283485 A1 | 11/2012 | Hasyagar et al. |
| 2013/0035441 A1 | 2/2013 | De Brouwer et al. |
| 2013/0094179 A1 | 4/2013 | Dai et al. |
| 2013/0108820 A1 | 5/2013 | Belfadhel et al. |
| 2013/0200415 A1 | 8/2013 | Evans et al. |
| 2013/0221837 A1 | 8/2013 | De Brouwer et al. |
| 2013/0270591 A1 | 10/2013 | De Brouwer et al. |
| 2014/0051802 A1 | 2/2014 | De Brouwer et al. |
| 2014/0051803 A1 | 2/2014 | De Brouwer et al. |
| 2014/0117393 A1 | 5/2014 | Van Heerbeek et al. |
| 2014/0192538 A1 | 7/2014 | Berix et al. |
| 2014/0339586 A1 | 11/2014 | Morizur et al. |
| 2015/0070933 A1 | 3/2015 | van Den Bogerd et al. |
| 2015/0318450 A1 | 11/2015 | De Brouwer et al. |
| 2016/0289377 A1 | 10/2016 | De Brouwer et al. |
| 2017/0025587 A1 | 1/2017 | Evans et al. |

FOREIGN PATENT DOCUMENTS

| | | |
|---|---|---|
| CN | 1339517 A | 3/2002 |
| CN | 101104803 A | 1/2008 |
| CN | 101205358 A | 6/2008 |
| CN | 101325238 A | 12/2008 |
| CN | 101885907 A | 11/2010 |
| CN | 102134383 A | 7/2011 |
| CN | 202091807 U | 12/2011 |
| DE | 102006016548 A1 | 10/2006 |
| EP | 0320658 A1 | 6/1989 |
| EP | 0475893 A1 | 3/1992 |
| EP | 0313165 B1 | 1/1993 |
| EP | 0523931 A2 | 1/1993 |
| EP | 0693470 B1 | 5/1998 |
| EP | 0885929 A1 | 12/1998 |
| EP | 0676237 B1 | 3/1999 |
| EP | 1160229 A1 | 12/2001 |
| EP | 1201303 A1 | 5/2002 |
| EP | 1234845 A2 | 8/2002 |
| EP | 1273563 A1 | 1/2003 |
| EP | 0788839 B1 | 5/2003 |
| EP | 1371623 A1 | 12/2003 |
| EP | 1459805 A1 | 9/2004 |
| EP | 1500671 A1 | 1/2005 |
| EP | 2143750 A1 | 1/2005 |
| EP | 1222960 B1 | 8/2005 |
| EP | 1808726 A1 | 7/2007 |
| EP | 1925874 A1 | 5/2008 |
| EP | 1520617 B1 | 2/2009 |
| EP | 2248841 A1 | 11/2010 |
| FR | 2685221 A1 | 6/1993 |
| FR | 2685323 A1 | 6/1993 |
| GB | 1377227 A | 12/1974 |
| JP | 5271132 A | 10/1993 |
| JP | 5294875 A | 11/1993 |
| JP | 5294876 A | 11/1993 |
| JP | 8038910 A | 2/1996 |
| JP | 08071433 A | 3/1996 |
| JP | 08319248 A | 12/1996 |
| JP | 08325185 A | 12/1996 |
| JP | 10211434 A | 8/1998 |
| JP | 10251180 A | 9/1998 |
| JP | 10314595 A | 12/1998 |
| JP | 10328573 A | 12/1998 |
| JP | 11179210 A | 7/1999 |
| JP | 11246458 A | 9/1999 |
| JP | 11255748 A | 9/1999 |
| JP | 2000281607 A | 10/2000 |
| JP | 2000281608 A | 10/2000 |
| JP | 2000319216 A | 11/2000 |
| JP | 2001233812 A | 8/2001 |
| JP | 2004149623 A | 5/2004 |
| JP | 2004231935 A | 8/2004 |
| JP | 2005037591 A | 2/2005 |
| JP | 2005048154 A | 2/2005 |
| JP | 2005082713 A | 3/2005 |
| JP | 2005115051 A | 4/2005 |
| JP | 2006124600 A | 5/2006 |
| JP | 2006339033 A | 12/2006 |
| JP | 2008184482 A | 8/2008 |
| JP | 2011029051 A | 2/2011 |
| KR | 20110033772 A | 3/2011 |
| OM | 101358133 A | 2/2009 |
| WO | 9209550 A1 | 6/1992 |
| WO | 9708122 A1 | 3/1997 |
| WO | 0050372 A1 | 8/2000 |
| WO | 0059853 A1 | 10/2000 |
| WO | 2008100165 A1 | 8/2008 |
| WO | 2011082204 A1 | 7/2011 |
| WO | 2011134674 A1 | 11/2011 |
| WO | 2012135584 A2 | 10/2012 |
| WO | 2012150559 A1 | 11/2012 |
| WO | 2012150560 A1 | 11/2012 |
| WO | 2013021332 A1 | 2/2013 |
| WO | 2013061274 A1 | 5/2013 |
| WO | 2014066784 A1 | 5/2014 |

OTHER PUBLICATIONS

Anonymous, "Polycarbonate preparation with a low yellowness index," Research Disclosure, Mason Publications, Hampshire GB vol. 449, No. 49 (Sep. 1, 2001) ISSN: 0374-4353 pp. 1-3.

Brunelle, D.J.: "Polycarbonates", Encyclopedia of Polymer Science and Technology, Jan. 1, 2006, pp. I.1-33, XP002525090, DOI: 10.1002/0471440264PST255.PUB2, Retrieved from the Internet: URL: http://mrw.interscience.wiley.com/emrw/9780471440260/epst/article/p.

Brydia; "Determination of Bisphenol A and Impurities by Gas Chromatography of Their Trimethylsilyl Ether Derivatives" Analytical Chemistry; vol. 40, No. 14; 1968; pp. 2212-2215.

Chan et al, "Facile Quantitative Analysis of Hydroxyl End Groups of Poly (2,6-dimethyl-1,4-phenylene oxide)s by 31P NMR Spectroscopy", Macromolecules (1994), vol. 27, pp. 6371-6375.

Chinese Patent No. 101885907 (A); Publication Date: Nov. 17, 2010; Abstract Only; 1 Page.

Chinese Patent No. 102134383 (A); Publication Date: Jul. 27, 2011; Abstract Only; 1 Page.

Chinese Patent No. 101205358 (A); Publication Date: Jun. 25, 2008; Abstract Only; 1 Page.

Chinese Patent No. 202091807 (U); Publication Date: Dec. 28, 2011; Abstract Only; 1 Page.

Chou et al.; "The Optimum Conditions for Solid-State-Prepared (Y3-xCex)Al5O12 Phosphor Using the Taguchi Method"; Advanced Powder Technology; vol. 12; 2012; pp. 97-103.

De Brouwer et al.; "Lexan* Polycarbonate for Optical Applications"; SABIC Innovative Plastics; Received Aug. 2, 2011; 5 Pages.

English Abstract of JP08038910(A); Date of Publication: Feb. 13, 1996; 1 Page.

English Abstract of JP08071433(A); Date of Publication: Mar. 19, 1996; 1 Page.

(56) References Cited

OTHER PUBLICATIONS

English Abstract of JP08325185(A); Date of Publication: Dec. 10, 1996; 2 Pages.
English Abstract of JP10211434(A); Date of Publication: Aug. 11, 1998; 2 Pages.
English Abstract of JP10251180(A); Date of Publication: Sep. 22, 1998; 1 Page.
English Abstract of JP10314595(A); Date of Publication: Dec. 2, 1998; 2 Pages.
English Abstract of JP10328573(A); Date of Publication: Dec. 15, 1998; 1 Page.
English Abstract of JP11179210(A); Date of Publication: Jul. 6, 1999; 2 Pages.
Abstract of JP11246458(A); Date of Publication: Sep. 14, 1999; 1 Page.
Abstract of JP11255748(A); Date of Publication: Sep. 21, 1999; 1 Page.
Abstract of JP2000281607(A); Date of Publication: Oct. 10, 2000; 1 Page.
Abstract of JP2000281608(A); Date of Publication: Oct. 10, 2000; 1 Page.
Abstract of JP2000319216(A); Date of Publication: Nov. 21, 2000; 1 Page.
Abstract of JP2001233812(A); Date of Publication: Aug. 28, 2001; 1 Page.
Abstract of JP5271132(A); Date of Publication: Oct. 19, 1993; 2 Pages.
Abstract of JP5294875(A); Date of Publication: Nov. 9, 1993; 2 Pages.
Abstract of JP5294876(A); Date of Publication: Nov. 9, 1993; 1 Page.
Factor et al.; "The Use of 31P NMR to Identify Color Bodies in y-irradiated Bisphenol-A Polycarbonate*"; Polymer Degradation and Stability; vol. 57; 1997; pp. 83-86.
Factor; "Search for the Sources of Color in Thermally Aged, Weathered and y-Ray Irradiated Bisphenol A Polycarbonate"; Die Angewandte Makromolekulare Chemie; vol. 232; 1995; pp. 27-43.
Godinez et al.; "Experimental Study of the Influence of Raw Material Impurities on Yellowness Index of Transesterification Polycarbonate"; Journal of Applied Polymer Science; vol. 119; 2011; pp. 1348-1356.
International Search Report; International Application No. PCT/US2013/028019; International Filing Date: Feb. 27, 2013; Dated Aug. 29, 2013; 7 Pages.
Japanese Patent No. 2004149623 (A); Publication Date: May 27, 2004; Abstract Only; 1 Page.
Japanese Patent No. 2004231935 (A); Publication Date: Aug. 19, 2004; Abstract Only; 1 Page.
Japanese Patent No. 2005037591 (A); Publication Date: Feb. 10, 2005; Abstract Only; 2 Pages.
Japanese Patent No. 2005048154 (A); Publication Date: Feb. 24, 2005; Abstract Only; 1 Page.
Japanese Patent No. 2005082713 (A); Publication Date: Mar. 31, 2005; Abstract Only; 2 Pages.
Japanese Patent No. 2005115051 (A); Publication Date: Apr. 28, 2005; Abstract Only; 1 Page.
Japanese Patent No. 2006339033 (A); Publication Date: Dec. 14, 2006; Abstract Only; 2 Pages.
Japanese Patent No. 2008184482 (A); Publication Date: Aug. 14, 2008; Abstract Only; 1 Page.
Japanese Patent No. 2011029051 (A); Publication Date: Feb. 10, 2011; Abstract Only; 2 Pages.
Li et al.; "Design of Mechanically Robust High-Tg Polymers: Synthesis and Dynamic Machanical Relaxation Behavior of Glassy Poly(ester carbonate)s with Cyclohexylene Rings in the Backbone"; Macromolecules; vol. 36; 2003; pp. 9411-9420.
Liptak et al.; "Absolute pKa Determination for Substituted Phenols"; J. Am. Chem. Soc.; vol. 124; 2002; pp. 6421-6427.
Machine Translation of FR2685221(A1); Date of Publication: Jun. 25, 1993; 26 Pages.
Machine Translation of FR2685323(A1); Date of Publication: Jun. 25, 1993; 26 Pages.
Machine Translation of JP08319248(A); Date of Publication: Dec. 3, 1996; 8 Pages.
Nowakowska et al.; "Studies of Some Impurities in Commercial Bisphenol-A"; Polish Journal of Applied Chemistry; vol. XL, No. 3; 1996; pp. 247-254.
Poskrobko et al.; "High-Performance Liquid Chromatography with Multi-Wavelength Detection of the Bisphenol A Impurities"; Journal of Chromatography A; vol. 883; 2000; pp. 291-297.
Written Opinion of the International Searching Authority; International Application No. PCT/US2013/028019; International Filing Date: Feb. 27, 2013; Dated Aug. 29, 2013; 17 Pages.
Chinese Patent No. 1204664(A); Date of Publication: Jan. 13, 1999; Machine Translation; 10 Pages.
Machine Translation of CN101104803(A); Date of Publication: Jan. 16, 2008; 6 Pages.
Machine Translation of CN101325238A; Date of Publication: Dec. 17, 2008; 13 Pages.
Machine Translation of CN101358133A; Date of Publication: Feb. 4, 2009; 12 Pages.
Machine Translation of CN1279231A; Date of Publication: Jan. 10, 2001; 7 Pages.
Machine Translation of CN1339517A; Date of Publication: Mar. 13, 2002; 5 Pages.
XP002719190 Database WPI, Week 200636, Thomson Scientific, London, GB; AN2006-347219.

PLASTIC COMPOSITION COMPRISING A POLYCARBONATE MADE FROM LOW SULFUR BISPHENOL A, AND ARTICLES MADE THEREFROM

CROSS REFERENCE TO RELATED APPLICATIONS

The present application is a divisional of U.S. patent application Ser. No. 13/779,781, filed Feb. 28, 2013, which claims priority to U.S. Provisional Application Ser. No. 61/604,960, filed Feb. 29, 2012, the contents of which are incorporated hereby in reference.

BACKGROUND

This disclosure relates to polycarbonate formed from 2,2-bis (4-hydroxyphenyl)propane (bisphenol A, BPA) with reduced sulfur content, and containing conversion material chemistry, and articles made therefrom.

BPA is widely employed in the manufacture of polymeric materials, such as engineering thermoplastics. For example, BPA is a principle monomer used in the manufacture of polycarbonate. In order to be effective in producing high quality polycarbonate products, higher purity levels are needed of the raw material BPA. The word high in the context of BPA and polycarbonate refers to BPA and/or polycarbonate with lower sulfur levels as a result of the processes encompassed by this disclosure.

Bisphenols, such as BPA, are generally prepared by the electrophilic addition of aldehydes, or ketones such as acetone, to aromatic hydroxyl compounds such as phenol, in the presence of an acidic catalyst. These types of reactions are also referred to as acid catalyzed condensation reactions.

There is a long felt yet unsatisfied need for new and improved processes for producing bisphenol A, which processes could, for example, employ a sulfur containing promoter in the reaction due to its ability to increase reaction conversion and improve selectivity in producing BPA.

BRIEF DESCRIPTION

Herein, disclosed are processes for producing high quality bisphenol A with reduced sulfur content, according to embodiments.

In one embodiment, a light emitting device, comprises: a lighting element located in a housing, wherein the housing is formed from a plastic composition comprising: a polycarbonate formed from reacting, in the presence of a transesterification catalyst, a diaryl carbonate ester and a bisphenol A, wherein the bisphenol A has a sulfur concentration of 1 ppm to 15 ppm, based upon a weight of the bisphenol A; and a conversion material wherein the conversion material comprises an inorganic material that converts radiation of a certain wavelength and re-emits of a different wavelength; wherein after the conversion material has been exposed to an excitation source, the conversion material has a luminescence lifetime of less than $10^{-4}$ seconds when the excitation source is removed.

In one embodiment, a plastic molded device having a transparency of greater than or equal to 30% measured according to ASTM D1003-00, Procedure B, illuminant C, on a spectrophotometer, and at a thickness of 1.04 mm, wherein the article is formed from the plastic composition comprises: a polycarbonate formed from reacting, in the presence of a transesterification catalyst, a diaryl carbonate ester and a bisphenol A, wherein the bisphenol A has a sulfur concentration of 1 ppm to 15 ppm, based upon a weight of the bisphenol A; and a conversion material wherein the conversion material comprises an inorganic material that converts radiation of a certain wavelength and re-emits of a different wavelength; wherein after the conversion material has been exposed to an excitation source, the conversion material has a luminescence lifetime of less than $10^{-4}$ seconds when the excitation source is removed The above described and other features are exemplified by the following figures and detailed description.

BRIEF DESCRIPTION OF THE DRAWINGS

Refer now to the figures, which are exemplary and non-limiting embodiments, and wherein the like elements are numbered alike.

DETAILED DESCRIPTION

One avenue for achieving the desired white light is to utilize conversion material chemistry in LED housings, specifically incorporating conversion materials throughout the LED housing, e.g., in close proximity to the LED. Conversion materials, e.g., luminescent materials, which emit light of longer wavelengths than that of the excitation source, include those having a solid inorganic host lattice doped with rare-earth elements. Conversion materials can be incorporated within a polymeric substrate by either coatings or being compounded directly into the polymer matrix during extrusion. However, such conversion materials are expected to degrade the polymer (e.g., polycarbonate) when incorporated into the polymer melt during extrusion. For example, polycarbonate melt stability is expected to decrease and the general color of the conversion material, before and during LED excitation will likely produce an undesirable effect. Loss of melt stability could lead to at least one of the following: embrittlement; undesirable resin color. Resin yellowing can affect correlated color temperature (downward shift), color rendering index; and decreased luminous efficacy. Furthermore, loss of melt stability could negatively affect the molder's ability to accurately mold a flat disk or sphere shaped optic, wherein the molded conversion material optic needs uniform surface features and reliable shrink properties for optimal light modeling (ray tracing), production quality, and angular color uniformity.

It is further noted that diminished flame retardant properties are anticipated in parts molded from degraded resin. As a result, luminaire designers will be limited while attempting to specify a plastic material with an inadequate UL rating, e.g., a thin wall flame retardancy is desired (e.g., a UL94 V0 rating at less than or equal to 1.5 millimeters (mm)).

Optimized polymer and conversion material and optical properties are needed so that the LED lighting products can meet Department of Energy (DOE) Energy Star rating using measurement methods described in IESNA LM-79 and IES LM-80-08. Thus, there is a need in the art to satisfy this requirement.

Figure 1:
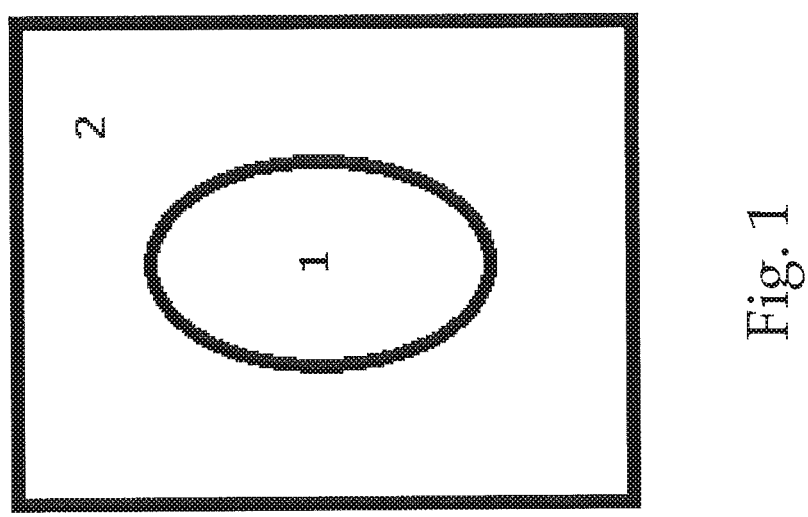
FIG. 1 depicts a light emitting device comprising a lighting element in a housing.

Some or all of the above needs can be met with a light emitting device comprising a lighting element 1 located in a housing 2, shown for example in FIG. 1, wherein the housing is formed from a plastic composition comprising a plastic material and a conversion material. The conversion material can, for example, absorb at least a portion of a first wavelength range radiation that is emitted from the light emitting device and emits radiation having a second wavelength range. This results in an altered light color perception by the viewer. For example, the conversion material can convert some of the blue light from a blue LED to yellow light and the overall combination of available light is perceived as white light to an observer. In this manner light emitting LEDs can effectively be tuned to result in different color than those immediately emitted from the LED. Further by incorporating the conversion material(s) into the plastic housing, industry requirements as well as processes that effectuate the manufacture of materials can be met.

A. Plastic Materials

Bisphenol A can be obtained by reacting acetone and phenol in the presence of a strong acid catalyst, such as hydrochloric acid (HCl) or a sulfonic resin and a sulfur containing promoter, e.g., a mercaptan promoter, such as methyl mercaptan (MM), ethyl mercaptan, 2,2-bis(methylthio)propane, mercaptocarboxylic acid, and/or 3-mercaptopropionic acid (3-MPA), as well as combinations comprising at least one of the foregoing.

In the absence of a sulfur containing promoter (such as 3-MPA), the reaction proceeds much slower and is less selective in producing bisphenol A (BPA). When we use the term "bisphenol A" or the abbreviation BPA, the compound with the systematic name 2,2-bis(4-hydroxyphenyl) propane is meant. Thus, the use of a sulfur containing promoter can increase reaction conversion and improve selectivity. However, although the use of a sulfur containing promoter in the reaction is desirable for at least the above reasons, the use of such as promoter can generate sulfur containing byproducts, and can result in sulfur being present in the bisphenol A product stream(s) thereby resulting in a reduction in BPA purity. High purity levels are needed of the raw material BPA in order to manufacture high quality polycarbonate products. Such sulfur also could result in sulfur based noxious smells in the resulting BPA products, as well as in the polycarbonate end product. Potential degradation, as well as color worsening also could occur in the BPA monomer and resultant polycarbonate polymer as a result of sulfur impurities.

Figure 2:
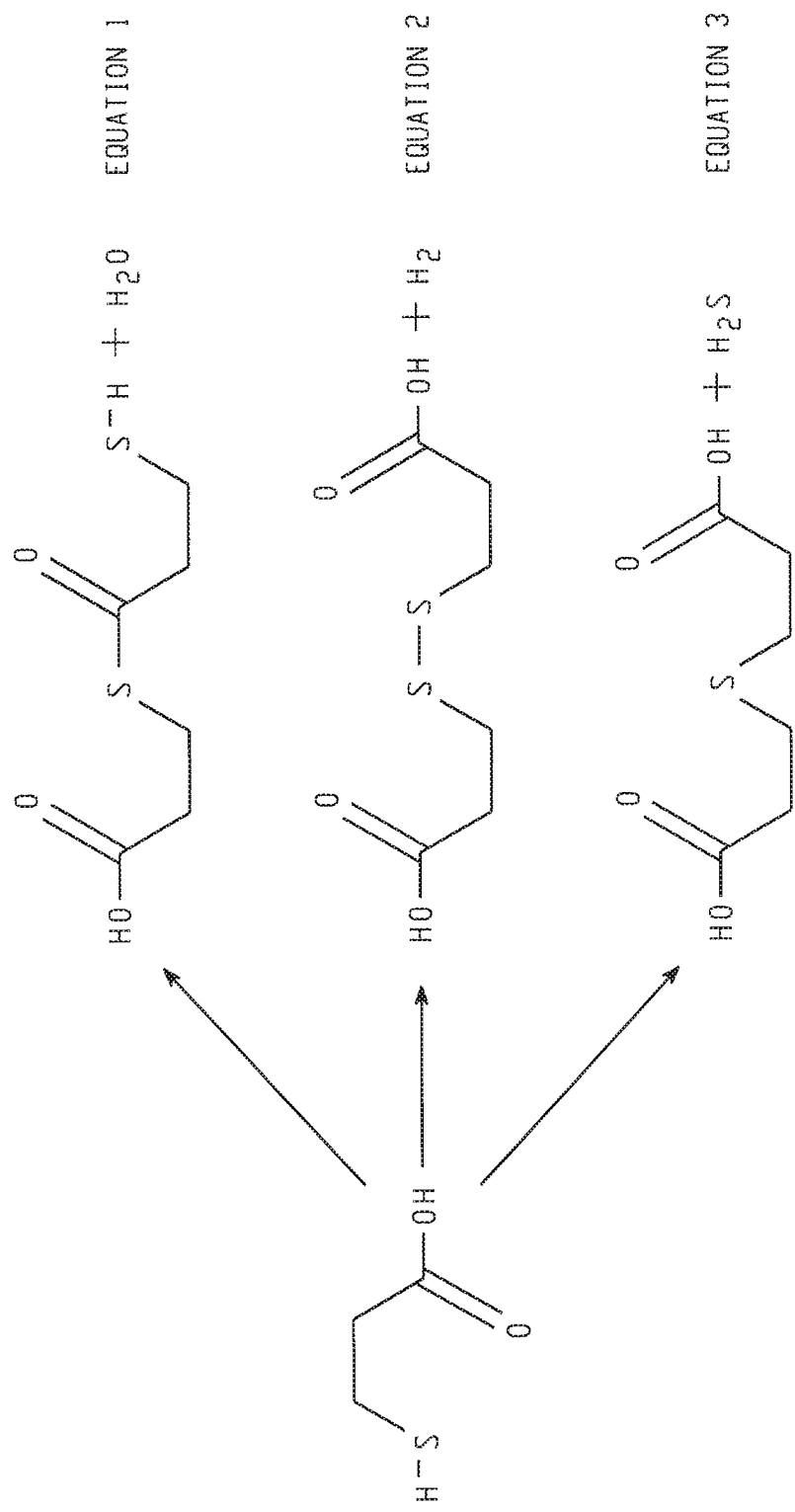
FIG. 2 depicts a schematic illustration of 3-MPA when used as a bulk promoter in a BPA ion exchange resin (IER) reaction can generate a series of by-products through side reactions.

In addition, sulfur compounds can be a source of odor issues during production of BPA and also during production of polycarbonate end products made from the BPA. A sulfur containing reaction promoter, such as 3-MPA, is an effective promoter for BPA production processes. However, if some of the promoter (or sulfur containing byproducts derived from the promoter) proceeds with the monomer into the resin process, it can also react with the phosgene, diphenyl carbonate, or the BPA during polycarbonate production and thus some sulfur can undesirably become incorporated into the polymer backbone and hence remain in the final product. Not to be limited by theory, it has been determined, for example, that when 3-MPA reacts with BPA it can create an end cap that would be incorporated into the polymer. The dimer or trimer of 3-MPA, as well as the sulfide and disulfide of 3-MPA also can be incorporated into the polymer chain. FIG. 2 depicts a schematic illustration showing that when 3-MPA is used as a bulk promoter in a BPA ion exchange resin (IER) reaction, the 3-MPA can generate a series of side reactions, such as those referred to as equation 1 (dimer or trimer of 3-MPA) and equations 2 and 3 (sulfide and disulfide, respectively). The majority of sulfur species present in the polycarbonate are bound to the polymer chain either as a chain building block or as an end cap, as opposed to being in a soluble state. Thus, during extrusion of polycarbonate the heat could generate a transesterification in the presence of moisture that could result in an undesirable release of odor through the release of 3-MPA or 3-MPA degradation products. Once the sulfur is incorporated into the BPA monomer, or incorporated into the polycarbonate polymer, the sulfur impurities cannot be removed by filtration or washing. Thus, a problem encountered is how to produce high purity BPA using effective reaction promoters, such as 3-MPA, while avoiding undesirable degradation of the BPA monomer and release of odor. It would be particularly desirable to obtain a method where sulfur could be removed downstream in the process, as opposed to being removed in the initial reaction section where phenol and acid can react together with a catalyst because in the initial reaction section sufficient amounts of sulfur are needed to execute the reaction. Moreover, it would be desirable to obtain such a method of sulfur removal wherein a promoter, such as 3-MPA, could be employed to achieve a high purity BPA product, while avoiding major restructuring of existing processing equipment.

Disclosed herein is a method to remove sulfur from a process stream comprising BPA such as a BPA product stream, in order to produce a high purity BPA product, specifically, how to, for example, remove sulfur impurities that have been incorporated into the BPA without destroying the monomer.

According to embodiments, and as described in further detail below, the addition of a base to the BPA product stream at elevated temperatures, such as temperatures greater than or equal to 50° C., typically between 80° C. and 100° C., can result in a significant reduction in organic sulfur concentration in the BPA. Thus, according to embodiments, sulfur is removed downstream in the BPA process, as opposed to removing sulfur in the reaction section. More particularly, sulfur can be removed from a liquid stream comprising BPA and phenol (derived from melting a slurry of a crystallized adduct of BPA and phenol), where the sulfur is present at lower levels than in the upstream sections or initial reaction vessel of the process. Such removal of sulfur downstream in the process is beneficial for creating a high purity BPA product, as well as a high purity polycarbonate end product made from the purified BPA. Moreover, embodiments can employ a sulfur based promoter in the process and thus avoid complex adaptations and potential reconfigurations of processing equipment and processing parameters. Thus, processes can be tailored to existing BPA plants where sulfur containing promoters can be employed.

A BPA process 10 will now be described with reference to the exemplary and non-limiting process flow diagram depicted in FIG. 3. In a formulation vessel 12, a mixture can be made that is effective for conducting the reaction: acetone 14 and phenol 16 are present as reactants in stream 60 to form BPA (e.g., 2 moles of phenol and one mole of acetone can react to form BPA plus water). An excess of phenol can be present since phenol also can optionally serve as a solvent for the BPA. The sulfur containing reaction promoter 18 can be added in stream 62 to facilitate the reaction. The promoter 18 can be added, for example, at levels of greater than or equal to 500 parts per million by weight (ppm), specifically, 1,000 ppm to 4,000 ppm, based upon the weight of the whole formulation. The promoter 18 can comprise a sulfur containing promoter such as set forth above. The temperature in the formulation vessel can be greater than or equal to 50° C., for example.

The formulation can be fed, for example, continuously to the reaction section 20 where it is heated to greater than or equal to 70° C. In the reaction section 20, an acid catalyst (e.g., inorganic and organic acids, such as sulfuric acid and hydrogen chloride, and cationic exchange resins, ion-exchange-resin (IER) (e.g., an acidic condensation catalyst, such as sulfonic resin, sulfuric acid, hydrochloric acid)), for example, can be present to help catalyze the reaction. The result is that, for example, the concentration of phenol and acetone goes down, the acetone concentration can decrease close to zero and thus the concentration of BPA can increase. Isomers, which are undesired, also can form, which are organic molecules in which acetone and phenol have reacted to form other than BPA. The reaction can take place at above room temperature, for example, 60° C.

Optionally, a co-promoter can be added to the reaction section 20. In various embodiments, the co-promoter (e.g. additional promoter added into the reaction) is different than the initial promoter already added to the reaction above. Examples of co-promoters include the above described sulfur containing promoters (namely, 3-MPA, methyl mercaptan, ethyl mercaptan, 2,2-bis(methylthio)propane, mercaptocarboxylic acid (e.g., mercaptopropionic acid)), promoter-bound resins (including resins ionically-bound to quaternary amine groups contained in mercaptoalkylpyridines and/or mercaptoalkylamines, the latter including 2-mercaptoethylamine derived from hydrolysis of 2,2 dimethylthiozolidine), as well as combinations comprising at least one of any of the foregoing. The co-promoters can be present, for example, to enhance selectivity in forming BPA, and to help obtain lower levels of the isomers.

The reaction mixture, which comprises acetone, phenol, BPA, sulfur and traces of isomers and promoter, can then flow in stream 66 to the crystallization section 22 where the mixture can be cooled to a temperature where crystals comprising BPA and phenol form. For example, the temperature can be less than or equal to 45° C. The crystals can be a BPA/phenol adduct. It is noted that "adduct" as used herein refers to the physical association of BPA and phenol (e.g., one molecule of BPA and one molecule of phenol can crystallize together to form a 1:1 molar ratio of BPA/phenol adduct).

Water 24 can optionally be added in stream 68 to the crystallization section 22, e.g., before crystallization to increase the rate of the crystallization process. The amount of water can be up to 3 weight percent (wt %), specifically, 0.1 to 3 wt % based upon a total weight of the mixture in the crystallization section 22. The stream exiting the crystallization section 22 (stream 70) can comprise a liquid phase and a solid phase.

In the filtration section 26, the liquid phase, stream 38 (e.g., mother liquor) can be separated from the solid phase, stream 80, which comprises the BPA/phenol crystals. Additional phenol from stream 27 and/or stream 32 can optionally be added to the filtration section 26 to wash the crystals.

Regarding the solid phase, this phase can comprise the BPA/phenol (PhOH) crystals, phenol, and traces of the isomers, and promoter. Typically, the solid phase, which is in the form of a slurry, can comprise, for example, up to 30 wt % of phenol. From the filtration section 26, the solid phase enters melting section 28 via slurry stream 80. Addition of phenol to the filtration section 26 also facilitates the melting of the crystals at a lower temperature.

Thus, this slurry stream 80 comprising the crystals can then become molten by heating (e.g., at 80° C.) in the melting section 28. The resulting molten stream can comprise a promoter, a solution of BPA in phenol, sulfur containing by-products, and possibly isomers. For example, the molten stream can comprise 50 wt % to 85 wt % BPA, specifically, 50 wt % to 75 wt % BPA, and more specifically, 55 wt % to 70 wt % BPA, based upon a total weight of the molten stream 82.

It has been determined that sulfur impurities can be removed from a stream comprising BPA and located downstream from an initial reaction section, e.g., a BPA product stream, instead of, for example, changing the sulfur containing promoter for an alternative technology. For example, a sulfur removal unit 54 could be located downstream of melting section 28 and upstream of a phenol desorption unit 30 (e.g., between the melting unit 28 and phenol desorption unit 30) without adversely affecting the other existing units or their operation. Therefore stream 82 exiting the melting section 28 can be directed to the sulfur removal unit 54. Since the molten stream 82 is at an elevated temperature, e.g., a temperature of greater than or equal to 70° C. to 120° C., the conditions are effective for sulfur removal while being sufficiently mild such that thermal degradation of the BPA is avoided.

Reduction of the concentration of sulfur impurities in the molten stream 82 comprises contacting the stream with a base in the sulfur removal unit 54. Employing the base treatment to molten stream 82, prior to the stream entering the phenol desorption unit 30 (e.g., evaporation unit), which is at a high temperature (e.g., greater than or equal to 200° C.) and under vacuum conditions, can be effective as the conditions prior to entering the desorportion unit 30 are more mild and conducive to sulfur removal. More particularly, after the phenol is evaporated off in the desorportion unit 30, a solid will be obtained or a product needing a higher temperature to remain liquid. In contrast, the BPA/phenol crystals can be melted and maintained molten, for example, at a temperature of 70° C. to 120° C., more specifically, 80° C. to 100° C. Under these mild conditions, the bases, e.g., resin bases, can remove the sulfur without becoming unstable and degrading. For example, generally, the resin bases are unstable and degrade when contacted with molten BPA at a temperature of greater than or equal to 200° C.

Figure 3:
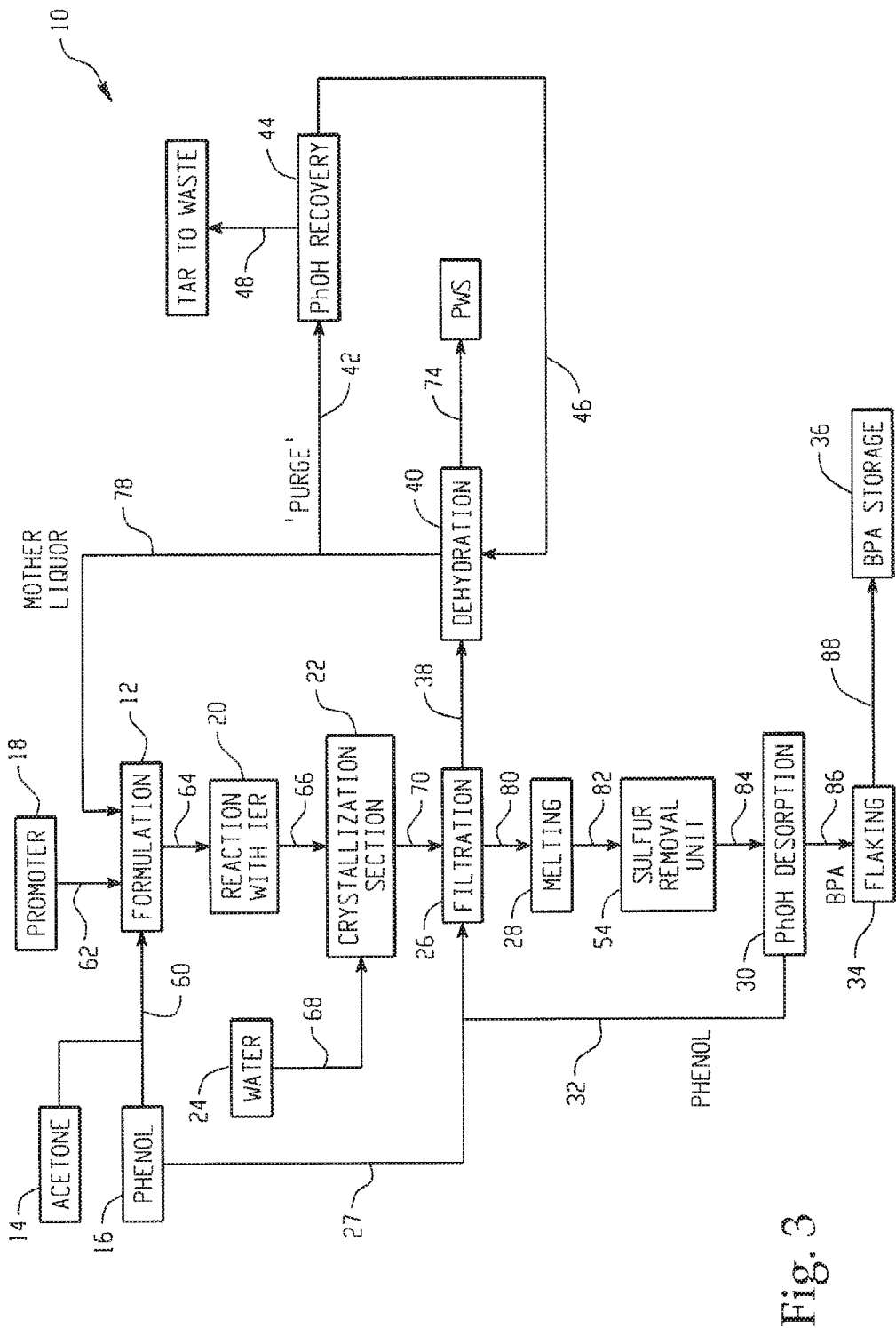
FIG. 3 depicts a BPA production process flow diagram using a single adduct crystallization.
Figure 4:
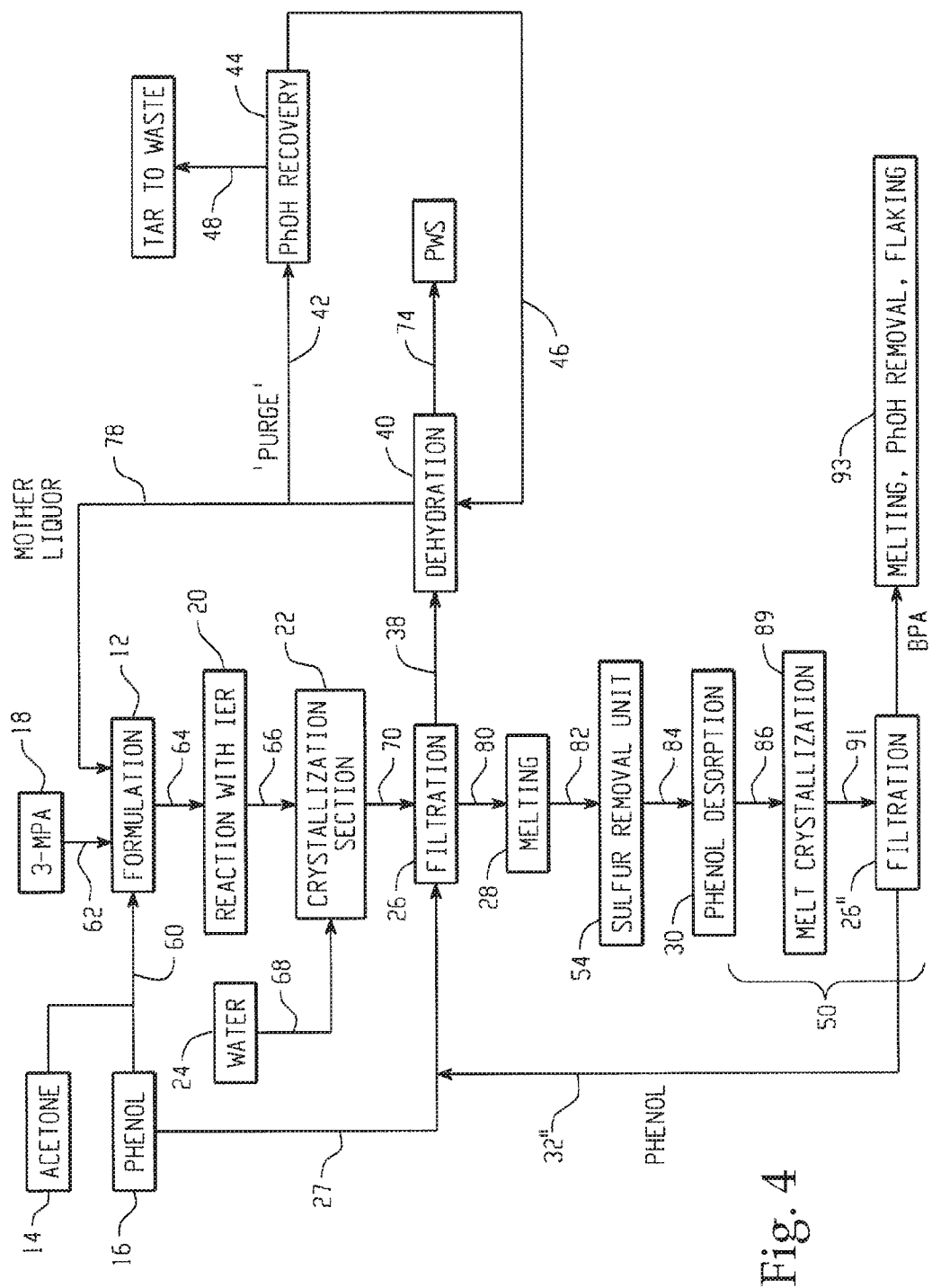
FIG. 4 depicts a BPA production process flow diagram using a double crystallization.

Thus, molten stream 82, which comprises BPA, phenol, and sulfur (e.g., sulfur containing by-products), can enter the sulfur removal unit 54 located upstream from the desorption unit 30, as shown in FIGS. 2, 3, and 4. Optionally, the BPA of stream 82 can be dissolved in a solvent prior to treating the stream with a base. Examples of solvents include, but are not limited to, methanol, hexane, diethyl ether, carbon tetrachloride, tetrahydrofuran, chloroform, acetone, acetonitrile, additional phenol, and so forth, as well as combinations comprising at least one of the foregoing.

Optionally, an alkali solution, such as potassium hydroxide, sodium hydroxide, and/or other (earth)alkali metal hydroxide(s) can be added to the molten stream 82 to form a mixture, exiting the melting section 28 to form a mixture to enable the reduction of sulfur in the mixture. For example, the mixture can be treated at temperatures up to the solvent boiling temperature for a period of time, e.g., greater than 10 minutes. According to embodiments, a treatment temperature of 70° C. to 90° C. (e.g., using solvent such as methanol), with a contact time of greater than or equal to 8 hours can result in a 95% reduction in organic sulfur concentration in the BPA. However, other treatment temperatures and contact times are possible depending upon, for example, the phenol content.

Additionally, or alternatively, the molten stream 82 exiting the melting section 28 can be treated with an anion exchange resin (e.g., in addition or alternative to the alkali solution) as the base. The treatment can be, for example, at a temperature near the solvent boiling temperature and below the anion exchange resin operating temperature, e.g., until sufficient amount of sulfur has been removed. For example, the treatment temperature can be 70° C. to 120° C., specifically, 80° C. to 100° C., as described above. Examples of anion exchange resins include, but are not limited to, AMBERLYST* A21, which is a tert-amine divinely benzene/styrene ion exchange copolymer commercially available from Dow, Lewatit MP 62 WS, a weakly basic macroporous anion exchange resin with tertiary amine groups on crosslinked polystyrene (e.g., commercially available from Lanxess, Tulsion A-8XMP), a basic macroporous anion exchange resin with tertiary amine functionality attached to crosslinked polystyrene (e.g., commercially available from Thermax), and a combination comprising at least one of the foregoing. It is noted that although an alkali solution can reduce the sulfur content in the BPA, it has further been determined that when an anion exchange resin is employed as the base, the BPA quality and the color of the BPA is even better than when the alkali solution is employed.

The sulfur removal unit 54 can, for example, be a packed bed column filled with the anion exchange resin. The molten stream 82 exiting the melting unit 28 and comprising the molten BPA can pass through the column. The conditions, for example, can be a contact time of greater than or equal to 10 minutes, specifically greater than or equal to 1 hour, at a temperature of 70° C. to 120° C., more specifically, 80° C. to 100° C. It is noted that treatment with the base can be in a batch, semi-batch, or continuous process.

Treatment of the molten stream 82 can reduce the sulfur content in the final BPA product to less than or equal to 15 ppm sulfur, specifically, 0.05 to 15 ppm sulfur, more specifically, 1 to 10 ppm sulfur, yet more specifically, 1 to 5 ppm sulfur, based upon the weight of the BPA product. For example, the sulfur content can be 2 to 10 ppm sulfur, based upon the weight of the BPA product.

From the sulfur removal unit 54, a twelfth stream 84 comprising BPA and phenol can enter phenol desorption unit 30. Optionally, phenol can be recycled from the phenol desorption unit 30 to the initial phenol supply 16 and/or to the filtration unit 26. Product stream 86 can exit the phenol desorption unit 30 and optionally proceed for further processing and/or storage. For example, the product stream 86 can optionally be processed in flaking section 34 and/or sent to storage section 36 via stream 88.

Figure 5:
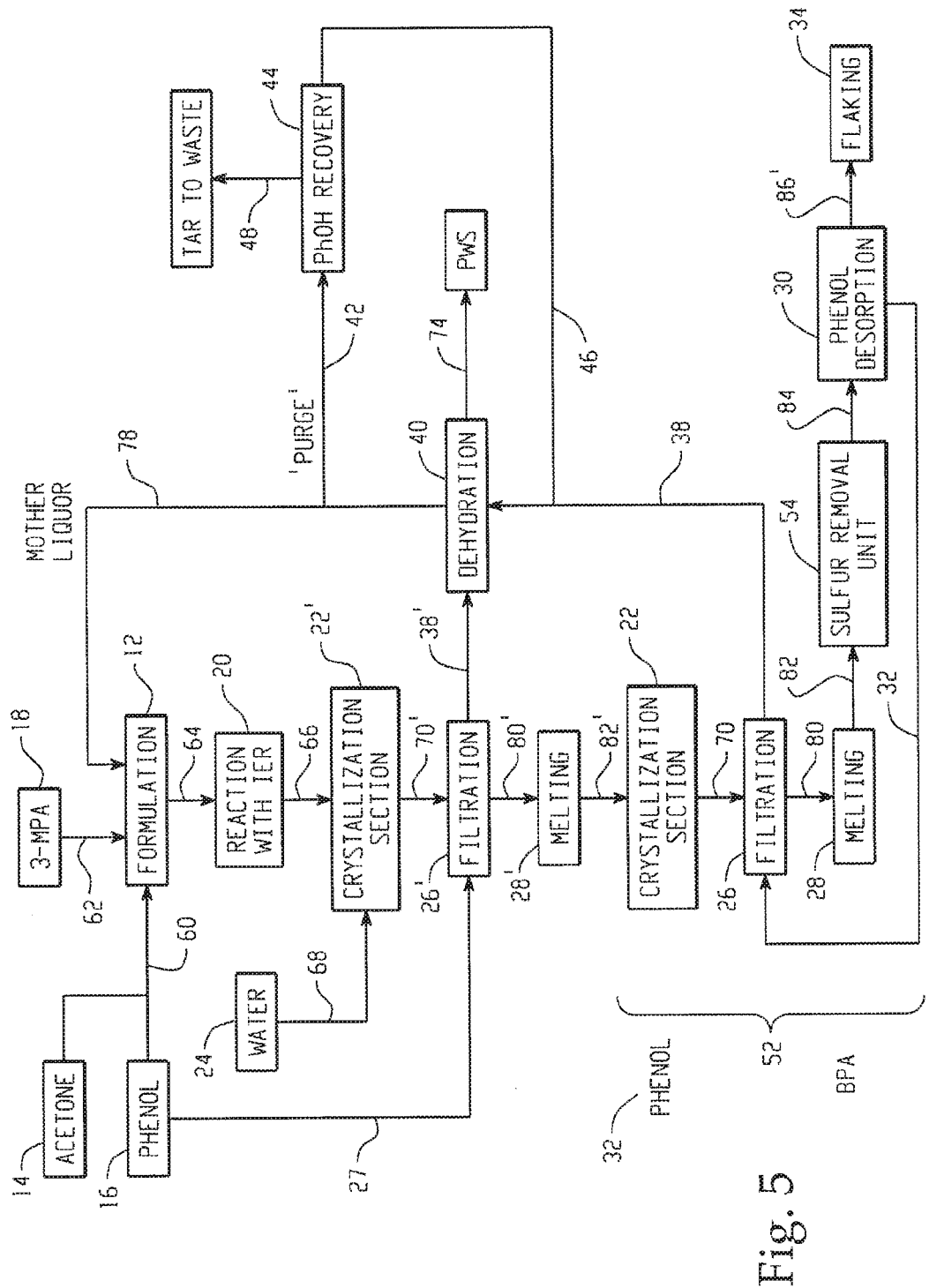
FIG. 5 depicts a BPA production process flow diagram using a double adduct crystallization.

Optionally, further processing of the various streams is possible, such as multiple crystallization cycles. For example, with reference to FIG. 5, the reaction mixture, which comprises acetone, phenol, BPA, sulfur and traces of isomers and promoter, can flow in stream 66 to the crystallization section 22' where the mixture can be cooled to a temperature where crystals comprising BPA and phenol form. For example, the temperature can be less than or equal to 45° C. Optionally, as noted above, water can be added to facilitate crystallization. From crystallization section 22, initial crystal stream 70', comprising a liquid phase and a solid phase, enters filtration section 26' where the liquid phase, stream 38' can be separated from the solid phase, stream 80'. Additional phenol from stream 27 and/or stream 32 can optionally be added to the filtration section 26' to wash the crystals.

The solid phase, stream 80' can then be melted in melting section 28' to form an initial molten stream 82'. This initial molten stream 82' can then be directed to the crystallization section 22 where it is crystallized and then further processed as described above. In such an arrangement, both liquid phase streams 38,38' can be directed to the dehydration section 40 and processed as described below.

FIG. 4 also illustrates a double crystallization, here, product stream 86 is further processed by directing the product stream 86 from the phenol desorption unit 30 into a melt crystallization unit 89 to form BPA crystals. The BPA crystals in phenol can be directed from the melt crystallization unit 89 via stream 91 to filtration unit 26" where phenol can optionally be removed and recycled via recycle stream 32", and stream 91 typically is in the form of a slurry (solid phase) comprising BPA crystals and phenol and can be further processed at section 93, e.g., melted, phenol removed, flaking, and/or storage.

The resultant BPA can be used in the production of BPA purified polycarbonate products. Accordingly, also disclosed in accordance with embodiments is a process of producing polycarbonate via in an interfacial or melt transesterification process. The polycarbonate can be formed into articles comprising reduced sulfur and characterized by virtually no sulfur based noxious smell. For example, the product can be a lighting device With further reference to FIGS. 2, 3, and 4, the liquid phase in stream 38,38' can be processed in the dehydration section 40. From this section 40, a stream 74 comprising water can proceed into the phenol-water separation (PWS) unit while a ninth stream 78 comprising the mother liquor can exit the dehydration section 40 and be fed back into formulation vessel 12 and/or be purged (stream 42). Purge stream 42 can enter phenol recovery station 44 where phenol is recovered and recycled via stream 46 while a tar stream 48 exits the phenol recovery station 44 and proceed to waste.

The bisphenol A product from this process can be used to form polycarbonate, e.g., in an interfacial polymerization or melt polymerization process. Although the reaction conditions for interfacial polymerization can vary, an exemplary process generally involves dissolving or dispersing the bisphenol A in aqueous caustic material (e.g., aqueous caustic soda or potash), adding the resulting mixture to a water-immiscible solvent medium, and contacting the reactants with a carbonate precursor in the presence of a catalyst such as triethylamine and/or a phase transfer catalyst, under controlled pH conditions, e.g., about 8 to about 12. The most commonly used water immiscible solvents include methylene chloride, 1,2-dichloroethane, chlorobenzene, toluene, and the like.

Generally, in the melt polymerization process, polycarbonates can be prepared by co-reacting, in a molten state, the bisphenol A and a diaryl carbonate ester, such as diphenyl carbonate, in the presence of a transesterification catalyst in a Banbury* mixer, twin screw extruder, or the like to form a uniform dispersion. Volatile monohydric phenol is removed from the molten reactants by distillation and the polymer is isolated as a molten residue. A specifically useful melt process for making polycarbonates uses a diaryl carbonate ester having electron-withdrawing substituents on the aryls. Examples of specifically useful diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis (4-methylcarboxylphenyl) carbonate, bis(2-acetylphenyl) carboxylate, bis(4-acetylphenyl) carboxylate, or a combination comprising at least one of the foregoing esters. Examples of transesterification catalysts include tetrabutylammonium hydroxide, methyltributylammonium hydroxide, tetrabutylammonium acetate, tetrabutylphosphonium hydroxide, tetrabutylphosphonium acetate, tetrabutylphosphonium phenolate, or a combination comprising at least one of the foregoing.

The polycarbonate can be formed from various materials such as one or more of those set forth in the following formulas:

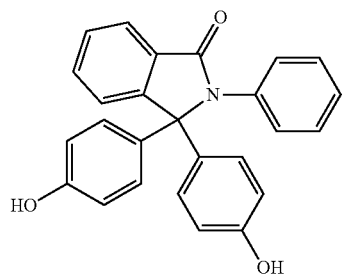
(1)

(also known as 3,3-bis(4-hydroxyphenyl)-2-phenylisoindolin-1-one (PPPBP)) also known as 2-phenyl-3,3-bis(4-hydroxyphenyl)phthalimidine;

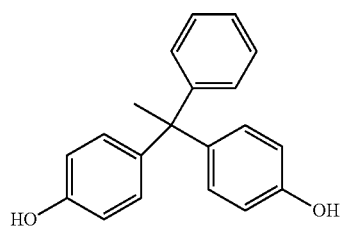
(2)

(also known as 4,4'-(1-phenylethane-1,1-diyl)diphenol (bisphenol AP) also known as 1,1-bis(4-hydroxyphenyl)-1-phenyl-ethane);

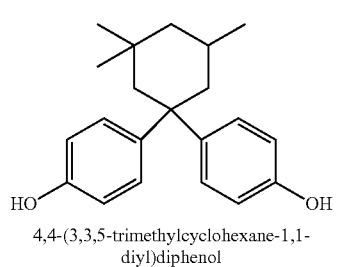
(3)
4,4-(3,3,5-trimethylcyclohexane-1,1-diyl)diphenol (bisphenol TMC) also known as 1,1-bis(4-hydroxyphenyl)-3,3,5-trimethylcyclohexane); adamantyl containing aromatic dihydroxy compounds and flourene containing aromatic dihydroxy compounds, Formulas (4) and (5) respectively;

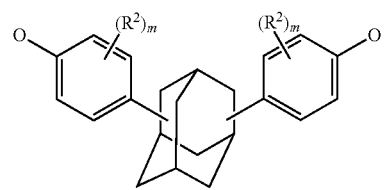
(4)

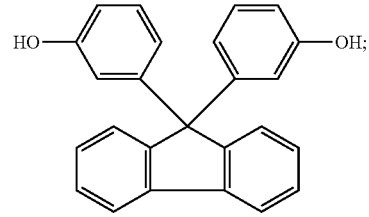
(5)

formula (6)

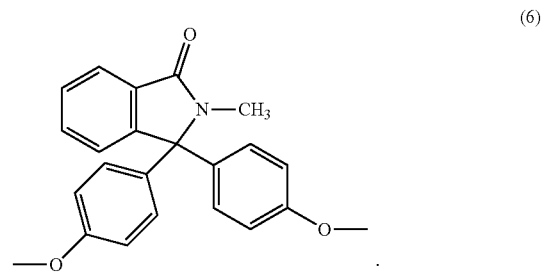
(6)

bisphenols containing substituted or unsubstituted cyclohexane units (e.g., bisphenols of formula (7))

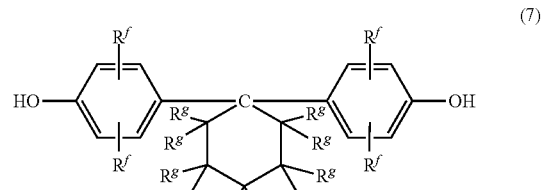
(7)

wherein each $R^f$ is independently hydrogen, $C_{1-12}$ alkyl, or halogen; and each $R^g$ is independently hydrogen or $C_{1-12}$ alkyl. The substituents can be aliphatic or aromatic, straight chain, cyclic, bicyclic, branched, saturated, or unsaturated. Cyclohexyl bisphenol containing polycarbonates, or a combination comprising at least one of the foregoing with other bisphenol polycarbonates, are supplied by Bayer Co. under the APEC® trade name.

"Polycarbonate" as used herein includes homopolycarbonates, copolymers comprising formula (8)

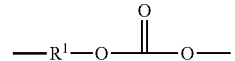
(8)

wherein different $R^1$ moieties in the carbonate (also referred to herein as "copolycarbonates"), and copolymers comprising carbonate units and other types of polymer units, such as ester units. More specifically, greater than or equal to 60%, particularly greater than or equal to 80% of the $R^1$ groups in the polycarbonate are derived from bisphenol A.

Another specific type of copolymer is a polyester carbonate, also known as a polyester-polycarbonate. Such copolymers further contain, in addition to recurring carbonate chain units of the formula (1), repeating units of formula (9):

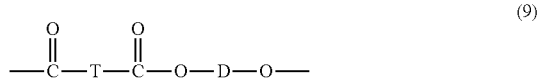
(9)

wherein D is a divalent group derived from a dihydroxy compound, and can be, for example, a $C_2$-$C_{10}$ alkylene group, a $C_6$-$C_{20}$ alicyclic group, a $C_6$-$C_{20}$ aromatic group or a polyoxyalkylene group in which the alkylene groups contain 2 to 6 carbon atoms, specifically 2, 3, or 4 carbon atoms; and T divalent group derived from a dicarboxylic acid, and can be, for example, a $C_2$-$C_{10}$ alkylene group, a $C_6$-$C_{20}$ alicyclic group, a $C_6$-$C_{20}$ alkyl aromatic group, or a $C_6$-$C_{20}$ aromatic group.

In one embodiment, D is a $C_2$-$C_{30}$ alkylene group having a straight chain, branched chain, or cyclic (including polycyclic) structure. In another embodiment, D is derived from an aromatic dihydroxy compound.

Examples of aromatic dicarboxylic acids that can be used to prepare the polyester units include isophthalic or terephthalic acid, 1,2-di(p-carboxyphenyl)ethane, 4,4'-dicarboxydiphenyl ether, 4,4'-bisbenzoic acid, and combinations comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or combinations thereof. A specific dicarboxylic acid comprises a combination of isophthalic acid and terephthalic acid wherein the weight ratio of isophthalic acid to terephthalic acid is 91:9 to 2:98. In another specific embodiment, D is a $C_{2-6}$ alkylene group and T is p-phenylene, m-phenylene, naphthalene, a divalent cycloaliphatic group, or a combination thereof. This class of polyester includes the poly(alkylene terephthalates).

The molar ratio of ester units to carbonate units in the copolymers can vary broadly, for example 1:99 to 99:1, specifically 10:90 to 90:10, more specifically 25:75 to 75:25, depending on the desired properties of the final composition.

In a specific embodiment, the polyester unit of a polyester-polycarbonate can be derived from the reaction of a combination of isophthalic and terephthalic diacids (or derivatives thereof) with resorcinol. In another specific embodiment, the polyester unit of a polyester-polycarbonate is derived from the reaction of a combination of isophthalic acid and terephthalic acid with bisphenol-A. In a specific embodiment, the polycarbonate units are derived from bisphenol A. In another specific embodiment, the polycarbonate units are derived from resorcinol and bisphenol A in a molar ratio of resorcinol carbonate units to bisphenol A carbonate units of 1:99 to 99:1.

A specific example of a polycarbonate-polyester is a copolycarbonate-polyester-polysiloxane terpolymer comprising carbonate units of formula (8), ester units of formula (9), and polysiloxane (also referred to herein as "polydiorganosiloxane") units of formula (10):

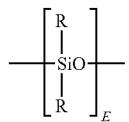
(10)

wherein each occurrence of R is same or different, and is a $C_{1-13}$ monovalent organic group. For example, R may independently be a $C_{1-13}$ alkyl group, $C_{1-13}$ alkoxy group, $C_{2-13}$ alkenyl group, $C_{2-13}$ alkenyloxy group, $C_{3-6}$ cycloalkyl group, $C_{3-6}$ cycloalkoxy group, $C_{6-14}$ aryl group, $C_{6-10}$ aryloxy group, $C_{7-13}$ arylalkyl group, $C_{7-13}$ arylalkoxy group, $C_{7-13}$ alkylaryl group, or $C_{7-13}$ alkylaryloxy group. The foregoing groups may be fully or partially halogenated with fluorine, chlorine, bromine, or iodine, or a combination thereof. Combinations of the foregoing R groups may be used in the same copolymer. In an embodiment, the polysiloxane comprises R groups that have a minimum hydrocarbon content. In a specific embodiment, an R group with a minimum hydrocarbon content is a methyl group.

The value of E in formula (10) may vary widely depending on the type and relative amount of each component in the plastic (e.g., thermoplastic) composition, the desired properties of the composition, and like considerations. Herein, E has an average value of 5 to 200, with the specific amount chosen so that a 1.0 mm thick plaque of the plastic composition (i.e., plastic material, conversion material(s), any additive(s)) has a transparency (% T) of greater than or equal to 30%. It is readily understood by an artisan that the E value is chosen (e.g., adjusted such as when the amount of siloxane in the material and when the siloxane is introduced to form the material and/or the process for making the material) to achieve a balance between transparency, flame retardancy, and impact. In an embodiment, E has an average value of 16 to 50, specifically 20 to 45, and more specifically 25 to 45. In another embodiment, E has an average value of 4 to 15, specifically 5 to 15, more specifically 6 to 15, and still more specifically 7 to 12.

In an embodiment, polydiorganosiloxane units are derived from dihydroxy aromatic compound of formula (11):

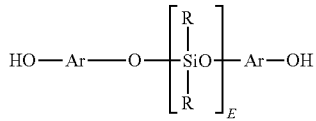
(11)

wherein E is as defined above; each R may independently be the same or different, and is as defined above; and each Ar may independently be the same or different, and is a substituted or unsubstituted $C_{6-30}$ arylene group, wherein the bonds are directly connected to an aromatic moiety. Suitable Ar groups in formula (11) may be derived from a $C_{6-30}$ dihydroxy aromatic compound, for example a dihydroxy aromatic compound of formula (2), (3), (7), or (8) above. Combinations comprising at least one of the foregoing dihydroxy aromatic compounds may also be used. Examples of dihydroxy aromatic compounds include resorcinol (i.e., 1,3-dihydroxybenzene), 4-methyl-1,3-dihydroxybenzene, 5-methyl-1,3-dihydroxybenzene, 4,6-dimethyl-1,3-dihydroxybenzene, 1,4-dihydroxybenzene, 1,1-bis(4-hydroxyphenyl) methane, 1,1-bis(4-hydroxyphenyl) ethane, 2,2-bis (4-hydroxyphenyl) propane, 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxyphenyl) cyclohexane, bis(4-hydroxyphenyl sulfide), and 1,1-bis(4-hydroxy-t-butylphenyl) propane. Combinations comprising at least one of the foregoing dihydroxy compounds may also be used. In an embodiment, the dihydroxy aromatic compound is unsubstituted, or is not substituted with non-aromatic hydrocarbon-containing substituents such as, for example, alkyl, alkoxy, or alkylene substituents.

In a specific embodiment, where Ar is derived from resorcinol, the polydiorganosiloxane repeating units are derived from dihydroxy aromatic compounds of formula (12):

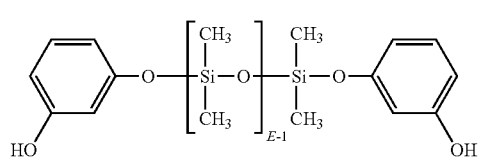

(12)

or, where Ar is derived from bisphenol-A, from dihydroxy aromatic compounds of formula (13):

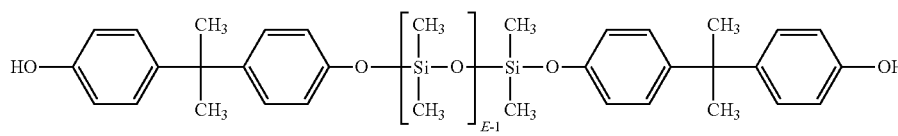

(13)

wherein E is as defined above.

In another embodiment, polydiorganosiloxane units are derived from dihydroxy aromatic compound of formula (14):

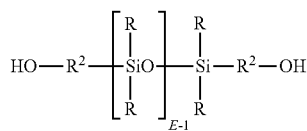

(14)

wherein R and E are as described above, and each occurrence of $R^2$ is independently a divalent $C_{1-30}$ alkylene or $C_{7-30}$ arylene-alkylene, and wherein the polymerized polysiloxane unit is the reaction residue of its corresponding dihydroxy aromatic compound. In a specific embodiment, where $R^2$ is $C_{7-30}$ arylene-alkylene, the polydiorganosiloxane units are derived from dihydroxy aromatic compound of formula (15):

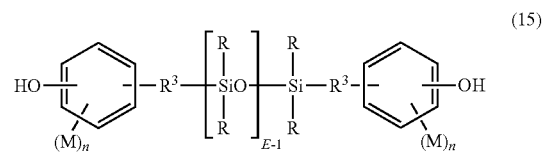

(15)

wherein R and E are as defined above. Each $R^3$ is independently a divalent $C_{2-8}$ aliphatic group. Each M may be the same or different, and may be a halogen, cyano, nitro, $C_{1-8}$ alkylthio, $C_{1-8}$ alkyl, $C_{1-8}$ alkoxy, $C_{2-8}$ alkenyl, $C_{2-8}$ alkenyloxy group, $C_{3-8}$ cycloalkyl, $C_{3-8}$ cycloalkoxy, $C_{6-10}$ aryl, $C_{6-10}$ aryloxy, $C_{7-12}$ arylalkyl, $C_{7-12}$ arylalkoxy, $C_{7-12}$ alkylaryl, or $C_{7-12}$ alkylaryloxy, wherein each n is independently 0, 1, 2, 3, or 4.

In an embodiment, M is bromo or chloro, an alkyl group such as methyl, ethyl, or propyl, an alkoxy group such as methoxy, ethoxy, or propoxy, or an aryl group such as phenyl, chlorophenyl, or tolyl; $R^3$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In another embodiment, R is methyl, or a combination of methyl and trifluoropropyl, or a combination of methyl and phenyl. In still another embodiment, M is methoxy, n is 0 or 1, $R^3$ is a divalent $C_{1-3}$ aliphatic group, and R is methyl.

In a specific embodiment, the polydiorganosiloxane units are derived from a dihydroxy aromatic compound of formula (16):

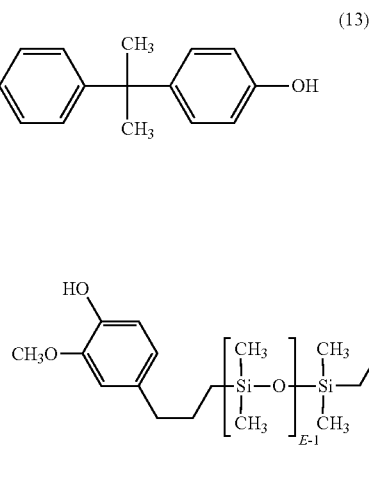

(16)

wherein E is as described above.

In another specific embodiment, the polydiorganosiloxane units are derived from dihydroxy aromatic compound of formula (17):

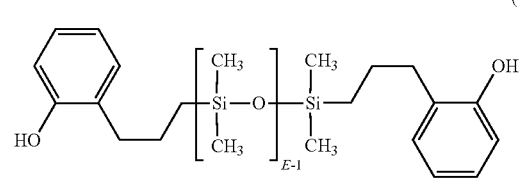

(17)

wherein E is as defined above.

Dihydroxy polysiloxanes typically can be made by functionalizing a substituted siloxane oligomer of formula (18):

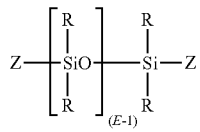

wherein R and E are as previously defined, and Z is H, halogen (Cl, Br, I), or carboxylate. Examples of carboxylates include acetate, formate, benzoate, and the like. In an exemplary embodiment, where Z is H, compounds of formula (18) may be prepared by platinum catalyzed addition with an aliphatically unsaturated monohydric phenol. Examples of aliphatically unsaturated monohydric phenols include eugenol, 2-allylphenol, 4-allylphenol, 4-allyl-2-methylphenol, 4-allyl-2-phenylphenol, 4-allyl-2-bromophenol, 4-allyl-2-t-butoxyphenol, 4-phenyl-2-allylphenol, 2-methyl-4-propenylphenol, 2-allyl-4,6-dimethylphenol, 2-allyl-4-bromo-6-methylphenol, 2-allyl-6-methoxy-4-methylphenol, and 2-allyl-4,6-dimethylphenol. Combinations comprising at least one of the foregoing may also be used. Where Z is halogen or carboxylate, functionalization may be accomplished by reaction with a dihydroxy aromatic compound. In an embodiment, compounds of formula (12) may be formed from an alpha, omega-bisacetoxypolydiorangonosiloxane and a dihydroxy aromatic compound under phase transfer conditions.

In some embodiments a copolycarbonate terpolymer can be used. Specific copolycarbonate terpolymers include those with polycarbonate units of formula (1) wherein $R^1$ is a $C_{6-30}$ arylene group, polysiloxane units derived from siloxane diols of formula (13), (16) or (17), and polyester units wherein T is a $C_{6-30}$ arylene group. In an embodiment, T is derived from isophthalic and/or terephthalic acid, or reactive chemical equivalents thereof. In another embodiment, $R^1$ is derived from the carbonate reaction product of a resorcinol of formula (8), or a combination of a resorcinol of formula (8) and a bisphenol of formula (4).

The relative amount of each type of unit in the foregoing terpolymer will depend on the desired properties of the terpolymer, and are readily determined by one of ordinary skill in the art without undue experimentation, using the guidelines provided herein. For example, the polycarbonate-polyester-polysiloxane terpolymer can comprise siloxane units in an amount of 0.1 to 25 weight percent (wt %), specifically 0.2 to 10 wt %, more specifically 0.2 to 6 wt %, even more specifically 0.2 to 5 wt %, and still more specifically 0.25 to 2 wt %, based on the total weight of the polycarbonate-polyester-polysiloxane terpolymer, with the proviso that the siloxane units are provided by polysiloxane units covalently bonded in the polymer backbone of the polycarbonate-polyester-polysiloxane terpolymer. The polycarbonate-polyester-polysiloxane terpolymer can further comprise 0.1 to 49.85 wt % carbonate units, 50 to 99.7 wt % ester units, and 0.2 to 6 wt % polysiloxane units, based on the total weight of the polysiloxane units, ester units, and carbonate units. Alternatively, the polycarbonate-polyester-polysiloxane terpolymer comprises 0.25 to 2 wt % polysiloxane units, 60 to 96.75 wt % ester units, and 3.25 to 39.75 wt % carbonate units, based on the total weight of the polysiloxane units, ester units, and carbonate units. The specific amount of terpolymer and the composition of the terpolymer will be chosen so that a 1.0 mm thick plaque of the composition transparency (% T) of greater than or equal to 30%.

B. Conversion Materials

Various types of conversion material(s) can be utilized in conjunction with a plastic (e.g., polycarbonate) containing composition described in this disclosure. Conversion material(s) are selected and added in an effective quantity so as to facilitate luminescence or transmission of an LED or other light-emitting device. The useful conversion material(s) have a shortlived luminescence lifetime of less than $10^{-4}$ seconds(s). It is noted that, depending upon how a conversion material is made, it may be longlived (luminescence lifetime of greater than minutes) or shortlived.

The conversion material(s) can be coated (e.g., result of applying a material to the surface of the conversion material(s), wherein the coating is on the surface and/or chemically interacts with the surface). Radiometric values (such as radiant power, radiant intensity, irradiance, and radiance) and corresponding photometric values (such as total luminance flux, luminous intensity, illuminance, luminance), luminance efficacy (in lumens per watt 1 m/W)), color rendering index, color quality scale (CQS), correlated color temperature, and chromaticity, are expected to improve compared to the uncoated conversion material(s) when added to a plastic material such as polycarbonate. Desirably, the conversion material(s) can be sufficiently coated so as to maintain melt stability with an MVR change of less than or equal to 30%, specifically less than or equal to 10% (i.e., MVR is determined at 6 minutes and again at 18 minutes, and the difference between these MVRs is less than or equal to 30% of the 6 minute value).

The conversion material(s) can be coated with silicone oil(s) and/or a layer of amorphous silica. Some examples of silicone oils include, but are not limited to: hydrogen-alkyl siloxane oil; polydialkyl siloxance oil; polydimethyl siloxane codiphenyl siloxane, dihydroxy terminated (such as Gelest PDS 1615 commercially available from Gelest, Inc.); as well as combinations comprising at least one of the foregoing. Such silicone oils are considered coatings where the conversion material is first treated with the silicone oil(s) prior to addition to a matrix or binder (collectively referred to as matrix), such as polycarbonate. The coating itself, is neither the binder nor the matrix that contains the conversion material to hold in place for exposure to blue LED radiation. Additionally, the coating does not require a curing method.

The conversion material can be coated with silicone oil e.g., by a method such as spraying the silicon oil. For example, the conversion material can be coated by spraying of the silicone oil in a fluidized bed reactor. The total amount of silicone oil can be 0.05 wt % to 20 wt % with respect to the conversion material, specifically, 0.1 wt % to 10 wt %, and more specifically, 0.5 wt % to 5 wt %, based upon the total weight of the conversion material. When two silicone coatings are used, such as polymethylhydrosiloxane and polydimethylsiloxane, the total amount does not change, and the split ratio between the two oils can be 1:99 to 99:1 depending on the type of protection being sought. In an embodiment, the first coating represents at least about 50 wt % of the total silicone oil content. Coating of conversion materials is further described in commonly assigned U.S. Pat. No. 6,692,659 B2 to Brown et al.

Some examples of oils include polymethylhydrosiloxane (for example, DF1040 commercially available from Momentive Performance Materials) and polydimethyl siloxane (e.g., DF581 commercially available from Momentive Performance Materials). Other examples include diphenyl siloxane, e.g., silanol terminated oils such as silanol terminated diphenylsiloxane (e.g., PDS-1615 commercially available from Gelest, Inc., Morrisville, Pa.). Loading level up to 4 pph by weight, specifically a loading of 0.1 to 0.5 (e.g., 0.2) pph by weight of pigment (e.g., Gelest PDS-1615). Other possible silanol terminated siloxanes include PDS-0338 and PDS-9931 also commercially available from Gelest, Inc. Desirably, the final article comprising the conversion material(s) comprises less than or equal to 20 pbw of conversion material(s) to 100 pbw of plastic material.

The conversion material(s), including those of which are surface treated, include: conversion material(s) having formula:

$$(A^3)_2SiO_4:Eu^{2+}D^1$$

where $A^3$ is a divalent metal selected from Sr, Ca, Ba, Mg, Zn, Cd, and combinations comprising at least one of the foregoing, and $D^1$ is a dopant selected from F, Cl, Br, I, P, S or N, and optionally combinations comprising at least one of the foregoing.

The conversion material(s) can be material(s) having formula: $(A^4)_2SiO_4:Eu^{2+}D^2$ with an optional dopant selected from Al, Co, Fe, Mg, Mo, Na, Ni, Pd, P, Rh, Sb, Ti or Zr, and optionally combinations comprising at least one of the foregoing, wherein $A^4$ is selected from Sr, Ba, Ca, and combinations comprising at least one of the foregoing.

The conversion material(s) can be material(s) having formula:

$$(YA^5)_3(AlB)_5(OD^3)_{12}:Ce^{3+} \quad (25)$$

where $A^5$ is a trivalent metal selected from Gd, Tb, La, Sm, or a divalent metal ion such as Sr, Ca, Ba, Mg, Zn, Cd, and combinations comprising at least one of the foregoing; B is selected from Si, B, P, and Ga, and optionally combinations comprising at least one of the foregoing; and $D^3$ is a dopant selected from F, Cl, Br, I, P, S or N, and optionally combinations comprising at least one of the foregoing. Other possible yellow conversion material(s) include: $Y_3Al_5O_{12}$:Ce; $Tb_{3-x}RE_xAl_5O_{12}$:Ce (TAG), wherein RE=Y, Gd, La, Lu; $Sr_{2-x-y}Ba_xCa_ySiO_4$:Eu; $Sr_{3-x}SiO_5$:Eu$^{2+}_x$, wherein 0<x≤1. Possible yellow/green conversion material(s) include: (Sr,Ca,Ba)(Al,Ga)$_2$S$_4$:Eu$^{2+}$; Ba$_2$(Mg,Zn)Si$_2$O$_7$:Eu$^{2+}$; Gd$_{0.46}$Sr$_{0.31}$Al$_{1.23}$O$_x$F$_{1.38}$:Eu$^{2+}_{0.06}$; (Ba$_{1-x-y}$Sr$_x$Ca$_y$)SiO$_4$:Eu; and Ba$_2$SiO$_4$:Eu$^{2+}$.

The conversion material(s) can be a material having the following formula: (YGd)$_3$Al$_5$O$_{12}$:Ce$^{3+}$ or Y$_3$Al$_5$(OD$^3$)$_{12}$:Ce$^{3+}$.

The conversion material(s) can be orange-red silicate-based conversion material(s) having formula:

$$(SrM1)_3Si(OD^4)_5:Eu$$

where M1 is selected from Ba, Ca, Mg, Zn, and combinations comprising at least one of the foregoing; and $D^4$ is selected from F, Cl, S, and N, and optionally combinations comprising at least one of the foregoing; conversion material(s); a Eu$^{2+}$ doped and or Dy$^{3+}$ conversion material(s) having formula:

$$M_3MgSi_2O_8$$

wherein M is selected from Ca, Sr, Ba and combinations comprising at least one of the foregoing.

The conversion material(s) can be red silicon nitride based Eu$^{2+}$ doped conversion material(s) having a formula:

$$(SrM2)_2Si_5N_8$$

where M2 is selected from Ca, Mg, and Zn. Other nitridosilicates, oxonitridosilicates, oxonitridoaluminosilicates examples include:

$$Ba_2SiN_8:Eu^{2+}$$

alpha-SiAlON:Re (Re=Eu$^{2+}$, Ce$^{3+}$, Yb$^{2+}$, Tb$^{3+}$, Pr$^{3+}$, Sm$^{3+}$), and optionally combinations comprising at least one of the foregoing.

$$Beta\text{-}SiAlON:Eu^{2+}$$

$$Sr_2Si_5N_8:Eu^{2+},Ce^{3+}$$

Rare earth doped red sulfate based conversion material(s), e.g., have the formula:

$$(SrM3)S$$

where M3 is selected from Ca, Ba, and Mg, and optionally combinations comprising at least one of the foregoing. Other possible red conversion material(s) include Sr$_x$Ca$_{1-x}$S:Eu,Y, wherein Y is a halide; CaSiAlN$_3$:Eu$^{2+}$; Sr$_{2-y}$Ca$_y$SiO$_4$:Eu; Lu$_2$O$_3$:Eu$^{3+}$; (Sr$_{2-x}$La$_x$)(Ce$_{1-x}$Eu$_x$)O$_4$; Sr$_2$Ce$_{1-x}$Eu$_x$O$_4$; Sr$_{2-x}$Eu$_x$CeO$_4$; SrTiO$_3$:Pr$^{3+}$,Ga$^{3+}$; CaAlSiN$_3$:Eu$^{2+}$; and Sr$_2$Si$_5$N$_8$:Eu$^{2+}$.

The conversion material(s) can comprise blue conversion material(s), e.g., having the formula BaMgAl$_{10}$O$_{17}$:Eu$^{2+}$.

The conversion material(s) can comprise green sulfate based conversion material(s), e.g., having formula:

$$(SrM3)(GaM4)_2S_4:Eu$$

where M3 is set forth above, and M4 is selected from Al and In.

The conversion material(s) can include Tb$_{3-x}$RE$^1_x$O$_{12}$:Ce (TAG), wherein RE$^1$ is selected from Y, Gd, La, Lu, and combinations comprising at least one of the foregoing; yttrium aluminum garnet (YAG) doped with cerium (e.g., (Y,Gd)$_3$Al$_5$O$_{12}$:Ce$^{3+}$; YAG:Ce); terbium aluminum garnet doped with cerium (TAG:Ce); silicate conversion material(s) (BOSE), (e.g. (Sr)$_2$SiO$_4$:Eu, (Ba)$_2$SiO$_4$:Eu, (Ca)$_2$SiO$_4$:Eu); nitride conversion material(s) (e.g., doped with cerium and/or europium); nitrido silicates (e.g., LaSi$_3$N$_5$:Eu$^{2+}$, O$^{2-}$ or Ba$_2$Si$_5$N$_8$:Eu$^{2+}$); nitride orthosilicate (e.g., such as disclosed in DE 10 2006 016 548 A1); or combinations comprising at least one of the foregoing. Other possible green conversion material(s) include: SrGa2S$_4$:Eu, Sr$_{2-y}$BaySiO$_4$:Eu, SrSiO$_2$N$_2$:Eu, and Ca$_3$Si$_2$O$_4$N$_2$:Eu$^{2+}$.

The various conversion material(s) described above can be used alone or in combination. The conversion material(s) can comprise combinations of yellow conversion material(s) (such as (Y,Gd)$_3$Al$_5$O$_{12}$:Ce3+ or (Sr,Ba,Ca)$_2$SiO$_4$:Eu) with a red conversion material(s) (such as (Sr,Ca)AlSiN$_3$:Eu), e.g., to produce a warm white light. The conversion material(s) comprise combinations of green aluminate (GAL) and a red conversion material(s) (e.g., to produce white light from the RGB of blue led, green light and red light). Green aluminate and red nitride conversion material(s) can be used alone or combined to generate white light when exposed to blue LED light. Red nitride conversion material(s) may contain ions to promote quantum efficiency. The conversion material(s) can comprise a combination of a semiconductor nanocrystals of cadmium sulfide mixed with manganese; and/or a La$_3$Si$_6$N$_{11}$:Ce$^{3+}$. A YAG:Ce conversion material or BOSE (boron ortho-silicate) conversion material, for example, can be utilized to convert the blue light to yellow. A reddish AlInGaP LED can be included to pull yellow light from the conversion material to the black body curve.

Also included are combinations comprising at least one of the foregoing conversion materials.

The YAG:Ce based conversion material(s) can be synthetic aluminum garnets, with garnet structure A$_3^{3+}$B$_5^{3+}$O$_{12}^{2-}$ (containing Al$_5$O$_{12}^{9-}$ and A is a trivalent element such as Y$^{3+}$). Specifically, in some embodiments, the conversion material(s) are not an aluminum spinel, wherein a spinel has the structure $A^{2+}B_2^{3+}O_4^{2-}$ ($Al_2O_4^{2-}$ and A is a divalent alkaline earth element such as $Ca^{2+}$, $Sr^{2+}$, and $Ba^{2+}$). The aluminum garnet is synthetically prepared in such a manner (annealing) as to impart short-lived luminescence lifetime lasting less than $10^{-4}$ seconds. Another process for forming short-lived luminescence (i.e., avoiding forming long afterglow materials) is disclosed in *Advanced Powder Technology* to Shii Choua et al., Volume 23, Issue 1, January 2012, Pages 97-103.

The amount of conversion material(s) added to a plastic material to form the plastic composition may vary according to the selected plastic composition and/or the surface coating for the selected conversion material(s). The conversion material(s) can be added to the plastic material in an amount of 0.1 to 40 parts by weight (pbw) of conversion material based on 100 pbw of plastic material, specifically, 4 to 20 pbw of conversion material(s) to 100 pbw of plastic material.

The conversion material(s) can have a median particle size of 10 nanometers (nm) to 100 micrometers (μm), as determined by laser diffraction. The median particle size is sometimes indicated as $D_{50}$-value. The median particle size can be 1 to 30 micrometers, specifically, 5 to 25 micrometers. Examples of median particle sizes include 1 to 5 micrometers, 6 to 10 micrometers, 11 to 15 micrometers, 16 to 20 micrometers, 21 to 25 micrometers, 26 to 30 micrometers, or 31 to 100 micrometers, or larger.

The plastic composition comprising conversion material(s) can take many different shapes. For example, the plastic composition comprising the conversion material(s) can have more or fewer bends such that it is U-shaped or V-shaped, or can have different bends with different radiuses of curvature. There can be multiple bends in different locations and different embodiments the plastic composition comprising the conversion material(s) can take more complex compound shapes. The plastic composition comprising the conversion material(s) can be rounded or polygonal, for example, the shape can be circular, oval, rectangular, square, pentagon, hexagon, octagon, etc., and/or it can have a more complex shape such as those illustrated in U.S. Patent Publication No. 2011/0140593 to Negley et al. Examples of some more complex shapes include hyperbolic paraboloid shapes, such as doubly ruled surface shaped like a saddle. Desirably, the radius of curvature for the different sections is such that there are no facing surfaces or the number of facing surfaces is minimized. The shape is generally open when viewed from the top. It is understood that the plastic composition comprising the conversion material(s) can take many different compound shapes beyond those described above. For example, a generally open shape comprising multiple edges and surfaces with different radiuses of curvature.

A silicone-coated conversion material(s) in polycarbonate is expected to maintain melt stability with an MVR change of less than or equal to 10% (i.e., MVR is determined at 6 minutes and again at 18 minutes, and the difference between these MVRs is less than or equal to 10% of the 6 minute value).

When testing the 6 minutes (min) MVR of a plastic composition (conversion material(s) (e.g., coated conversion material(s)) in a plastic material (e.g., polycarbonate (PC)) sample and comparing to the 6 min MVR of the plastic material (e.g., the same plastic material without the coated conversion material), the addition of the conversion material(s) (e.g., coated conversion material(s)) to plastic should change the 6 min MVR by less than or equal to 30%, specifically, less than or equal to 15%, and more specifically less than or equal to 5%. Similarly, the MVR of the 18 min dwell of the coated conversion material(s) plastic sample compared to the plastic material, should change by less than or equal to 30%, specifically less than or equal to 10%, and more specifically, less than or equal to 5%. It is also desirable to have a MVR change from the 6 min MVR of the coated conversion material(s) containing sample compared to the 18 min MVR for the same sample of less than or equal to 20%, specifically, less than or equal to 10%, and more specifically, less than or equal to 5%.

Notched Izod impact (% ductility) at 3.2 mm as determined according to ASTM D256-10 at room temperature (RT) of 23° C. and low temperature (e.g., 0° C.) can be greater than or equal to 80%, specifically, greater than or equal to 90%, and more specifically, 100%.

Lightness (L*) is expected to be greater as well as measured by CIELAB (Reflectance, with a D65 illuminant, and a 10 degree observer). Coated conversion materials will not scrub the inside of the extruder or injection molding machine. Scrubbing leads to graying of the resin and/or the final part. Any unintended color shift either due to resin yellowing or graying will lead to undesirable effects on the total luminous flux and chromaticity across the lifetime of a solid state lighting device. It is desirable to prevent the solid state lighting device from emitting different amounts of light and different colors through its life.

A stable resin system should enable higher reliability where the luminous flux and color coordinates shift is minor and allows greater lumen maintenance. Lumen maintenance may be evaluated according to IES LM-80-08 method, IES TM-21, IESNA methods or any other type of method used to determine lifetime of a solid state lighting product, but not limited to these methods.

A YAG:Ce conversion material or BOSE (boron orthosilicate) conversion material, for example, can be utilized to convert the blue light to yellow. A reddish AlInGaP LED can be included to pull yellow light from the conversion material to the black body curve. The conversion material can be arranged so that none or a minimal amount of heat from the LEDs passes into the conversion material to avoid heat degradation. The plastic composition can also be shaped to provide a uniform distribution of light from the lamp while minimizing absorption of re-emitted light. In one embodiment, the conversion material comprises YAG:Ce conversion material or BOSE conversion material and a red conversion material so that the lamp emits the desired CRI and color temperature.

The plastic composition can also have different characteristics to provide the desired emission pattern from the lamp. In some embodiments, the conversion material layer can have regions with different thickness, with the sections of greater thickness presenting more conversion material for the light to pass through. In other embodiments the article (e.g., housing) formed from the composition can have different concentrations of conversion materials in different regions. In other embodiments, the plastic composition can also have more than one conversion material mixed throughout, or can have different regions of different conversion materials. The conversion material can also have dispersing agents arranged throughout, or dispersing agents arranged in different concentrations in different regions. The plastic composition can also have regions that are substantially transparent.

C. Other Additives for Polycarbonate Compositions

The thermoplastic composition can include various additive(s) ordinarily incorporated in polycarbonate compositions of this type, with the proviso that the additives are selected so as to not significantly adversely affect the desired properties of the polycarbonate, for example, impact, viscosity, and flame retardance. Combinations of additives can be used. Such additives can be mixed at a suitable time during the mixing of the components for forming the composition.

The additive(s) can be selected from at least one of the following: UV stabilizing additives, impact modifiers, thermal stabilizing additives, flame retarding agents, mold release agents, colorants, melt stabilizers, scattering agents (such as titanium dioxide), organic and inorganic fillers, interference particles, color absorbing particles, gamma-stabilizing agents, and scattering particles, and/or diffusers (e.g., Tospearl 120 (also known as TSR9004 commercially available from Momentive Performance Materials), acrylic particles, and so forth). Epoxies, such as Joncryl* commercially available from BASF, for example could be added for melt stability.

For example, scattering particles, e.g., in a concentration of greater than 0 to 1 pbw, specifically, 0.001 pbw to 0.3 pbw, more specifically, 0.01 pbw to 0.2 pbw, based upon 100 pbw of plastic material. For some scattering particles there can be an increase in transmittance loss due to light absorption for higher concentrations. Thus, the concentrations of the scattering particles should be chosen in order to maintain an acceptable light absorption loss. The scattering particles can comprise many different materials including but not limited to: silica gel, zinc oxide (ZnO), yttrium oxide ($Y_2O_3$), titanium dioxide ($TiO_2$), barium sulfate ($BaSO_4$), alumina ($Al_2O_3$), fused silica ($SiO_2$), fumed silica ($SiO_2$), aluminum nitride, glass beads, zirconium dioxide ($ZrO_2$), silicon carbide (SiC), tantalum oxide ($TaO_5$), silicon nitride ($Si_3N_4$), niobium oxide ($Nb_2O_5$), boron nitride (BN), conversion material particles (e.g., YAG:Ce, BOSE), as well as combinations comprising at least one of the foregoing.

D. Blending/Processing Section

Plastic compositions (e.g., polycarbonate) can be manufactured by various methods. For example, a blend of various plastic compositions, e.g. polycarbonate can be fed into the throat of a single or twin-screw extruder via a hopper. Care must be taken so as to not effectuate shear of the conversion material(s) (e.g., coated conversion material(s)) and should limit pressure applied to conversion materials and/polycarbonate material so as to not affect its desired properties.

The final conversion material can be used in plastic material(s) (e.g., polycarbonate or any other thermoplastic resin formulation). During the plastic material's extrusion process, the conversion material(s) (e.g., coated conversion material(s)) can be added upstream or downstream using a side feeder. The conversion material(s) (coated conversion material(s)) can be added to the melt alone. Optionally, the conversion material(s) (coated conversion material(s)) can also be added directly to a blender and mixed with resin powder. The advantage of the coated conversion material(s) in this case is the reduction of the contacts between the abrasive conversion material(s) and the walls or the mixing elements, which reduces the graying issues in the final product and therefore leads to greater luminous flux and color quality in a solid state lighting device that produces white light.

The conversion material(s) (coated conversion material(s)) can first be compounded into polycarbonate with an appropriate heat stabilizer on a single screw or twin screw extruder in order to wet the surface for production (e.g., a master batch production). Multiple passes through an extruder may be necessary to fully wet the coated conversion material surface. Such master batches can then be added downstream or at the throat on a dedicated feeder(s) for accurate addition the final polymer formulation in an extruder. When added to the final polymer formulation, only mild distributive mixing is then used to fully disperse the coated conversion material(s) into the formulation. Examples of processing are further described in commonly assigned U.S. Pat. No. 6,692,659 B2 to Brown et al.

E. Article Section

Shaped, formed, or molded articles comprising the plastic (e.g., thermoplastic) compositions are also provided. The plastic compositions can be formed into useful shaped articles by a variety of means such as injection molding, extrusion (e.g., film/sheet extrusion), rotational molding, blow molding, and thermoforming.

In one embodiment, the plastic composition or polycarbonate containing compositions and the coated conversion material can be employed in a lighting type application, e.g., as a housing for an LED light.

In a further embodiment, the LEDs in a housing formed from the plastic composition can be employed in aviation lighting, automotive lighting, (e.g., brake lamps, turn signals, headlamps, cabin lighting, and indicators), traffic signals, text and video displays and sensors, a backlight of the liquid crystal display device, control units of various products (e.g., for televisions, DVD players, radios, and other domestic appliances), and a dimmable solid state lighting device.

An article (e.g., illumination device such as a light, luminaire, signal, and so forth) can comprise a semiconductor light-emitting element, which emits light (e.g., having a peak wavelength of 370 nm to 470 nm); and a light-emitting portion comprising the composition, wherein the light-emitting portion is excited by the light emitted from the semiconductor light-emitting element to emit light.

A lighting arrangement can comprise: a radiation source configured to emit radiation having a first wavelength range; a coated conversion material configured to absorb at least a portion of said first wavelength range radiation and emit radiation having a second wavelength range; and an optical component through which at least said first wavelength range radiation passes, wherein the coated conversion material contained with/dispersed in the optical component.

In a further embodiment, the conversion material is surface coated.

In any of the embodiments disclosed herein, the conversion material(s) can be coated with one or more surface coatings described in this disclosure.

In a further embodiment, the lighting arrangement can further comprise a radiation source, e.g., a light emitting diode (LED) or a light pipe. For example, the lighting arrangement can comprise an LED chip comprising a gallium nitride LED.

Optionally, the radiation source can be operable to emit radiation having a wavelength of 300 nanometers (nm) to 500 nm.

The conversion material can optionally be configured to emit radiation having a wavelength of 450 nm to 700 nm. Desirably, the conversion material emits at a different wavelength than the radiation source.

The lighting arrangement can comprise an optical component (e.g., a lens) having a surface that can be convex, concave, hemispherical, spherical, hollow cylinder, a paraboloid, and planar, as well as combinations comprising at least one of the foregoing. In the various embodiments, the coated conversion material(s) can be within the surface, e.g., can be mixed within the composition that forms the optical component. Optionally, a light diffusing material can be incorporated with the plastic composition. Examples of diffusing materials include: crosslinked polymethylmethacrylate (PMMA), polytetrafluoroethylene (Teflon), and methylsesquioxane (e.g., Tospearl 120 or TSR9004). The housing can be transparent to light from the light source and the coated conversion material, or can comprise a diffusing particle or a diffusing surface to help mix the light as it passes through the housing. Optionally, portions of the housing can be diffusive, while other portions can be transparent or clear.

In an embodiment, an optical component can be for a lighting arrangement of a type comprising a radiation source configured to emit radiation having a first wavelength range. The optical component can comprise a plastic and (e.g., throughout the optical component) a coated conversion material configured to absorb at least a portion of said first wavelength range radiation and emit radiation having a second wavelength range; and said optical component being configured such that at least said first wavelength range radiation passes though the optical component. The radiation source can be a LED (e.g., light emitting diode (LED) chip or die, light emitting polymers (LEPs), polymer light emitting diodes (PLEDs), organic light emitting diodes (OLEDs), or the like) and is a solid-state semiconductor device, which can convert electricity directly into light. For example, LED comprises a semiconductor chip, one side of the chip is attached to a stent, the end is negative ("n"), the other side connects to the positive ("p") terminal of the power. The whole chip can optionally be packaged (e.g., coated, encapsulated, and so forth). LEDs, e.g., in the form of an array, can be fashioned on a base (substrate or "PCB" printed circuit board) in thermal communication with a heat sink.

In other words, the semiconductor chip has two parts, one is p-type semiconductor and the other part is the n-type semiconductor. A p-n junction is formed between them when the two semiconductors are connected. An electrical path for supplying control signals to the LEDs can be provided through conductors. The conductors are electrical elements (e.g., strips) applied to a surface of an insulative layer. The insulative layer is mounted to a heat sink. The insulative layer can be a circuit board. The conductor may be any suitable electrically conductive material. Examples of electrically conductive materials include copper, aluminum, or the like, and combinations comprising at least one of the foregoing.

The current acting on the chip causes the emission of energy (e.g., in the form of photons). The wavelength of the light or the color is determined by the material of p-n junction.

In one embodiment, a process for producing a bisphenol A product comprises: reacting phenol with acetone in the presence of a sulfur containing promoter to obtain a reaction mixture comprising bisphenol A, phenol, and the promoter; after reacting the phenol with the acetone in the presence of the promoter, cooling the reaction mixture to form a crystal stream comprising crystals of bisphenol A and phenol (e.g., that contain sulfur); separating the crystals from the crystal steam; melting the crystals to form a molten stream of bisphenol A, phenol, and sulfur (e.g., promoter, sulfur containing by-products, etc.); contacting the molten stream with a base to reduce a sulfur concentration in the molten stream and form a reduced sulfur stream; and removing phenol from the reduced sulfur stream to form a bisphenol A product.

In the various embodiments, (i) the molten stream can be contacted with a base at a temperature of 70° C. to 120° C.; and/or (ii) the molten stream can be contacted with a base at a temperature of 80° C. to 100° C.; and/or (iii) the promoter can comprise a catalyst selected from 3-mercaptopropionic acid, methyl mercaptan, ethyl mercaptan, 2,2-bis(methylthio)propane, mercaptocarboxylic acid, and combinations comprising at least one of the foregoing promoters; and/or (iv) the promoter can comprise 3-mercaptopropionic acid; and/or (v) the base can comprise an alkali solution; and/or (vi) the base can comprise an anion exchange resin; and/or (vii) the anion exchange resin comprises a tert-amine divinylbezene/styrene ion exchange copolymer; and/or (viii) the process can further comprise adding additional phenol to the molten stream prior to contacting the stream with the base; and/or (ix) the sulfur concentration can be reduced to 0.5 ppm to 15 ppm based upon the weight of the bisphenol A; and/or (x) the sulfur concentration can be reduced to 2 ppm to 10 ppm based upon the weight of the bisphenol A; and/or (xi) the sulfur concentration can be reduced to 3 ppm to 8 ppm based upon the weight of the bisphenol A; and/or (xii) the process can further comprise, prior to forming the crystal stream, cooling the reaction mixture to form an initial crystal stream comprising initial crystals of bisphenol A and phenol, separating the initial crystals from the initial crystal stream, melting the initial crystals to form an initial molten stream, and then performing the cooling to form the crystal steam; and/or (xiii) the process can further comprise melt crystallizing the bisphenol A product.

Also included herein is polycarbonate made from the bisphenol A product of any of the above processes, as well as products made from the polycarbonate.

In one embodiment, a process for making polycarbonate, comprises: reacting, in the presence of a transesterification catalyst, a diary' carbonate ester and the bisphenol A product formed in any of the above methods, wherein the bisphenol A has a sulfur concentration of 1 ppm to 15 ppm, based upon a weight of the bisphenol A.

In another embodiment, a process for making polycarbonate, comprises: forming a mixture of the bisphenol A product from any of the above methods, in aqueous caustic material, wherein the bisphenol A has a sulfur concentration of 1 ppm to 15 ppm, based upon a weight of the bisphenol A; adding the mixture to a water-immiscible solvent medium; and contacting the reactants with a carbonate precursor in the presence of a catalyst to form the polycarbonate.

In one embodiment, a light emitting device comprises: a lighting element located in a housing, wherein the housing is formed from a plastic composition comprising: any of the polycarbonate formed by any of the processes disclosed above and a conversion material, the conversion material is optionally coated. The conversion material comprises: greater than 0 ppm of a first material selected from Si, Sr, Ba, Ca, Eu, and combinations comprising at least one of the foregoing first materials; and less than 50 ppm of a second material selected from Al, Co, Fe, Mg, Mo, Na, Ni, Pd, P, Rh, Sb, Ti, Zr, and combinations comprising at least one of the foregoing second materials. After the conversion material has been exposed to an excitation source, the conversion material has a luminescence lifetime of less than $10^{-4}$ seconds when the excitation source is removed.

In one embodiment, a plastic molded device has a transparency of greater than or equal to 30%, wherein the article is formed from the plastic composition. The plastic composition comprises the polycarbonate formed by any of the processes disclosed above and a conversion material, the conversion material is optionally coated. The conversion material comprises greater than 0 ppm of a first material selected from Si, Sr, Ba, Ca, Eu, and combinations comprising at least one of the foregoing first materials; and less than 50 ppm of a second material selected from Al, Co, Fe, Mg, Mo, Na, Ni, Pd, P, Rh, Sb, Ti, Zr, and combinations comprising at least one of the foregoing second materials. After the conversion material has been exposed to an excitation source, the conversion material has a luminescence lifetime of less than $10^{-4}$ seconds when the excitation source is removed.

In an embodiment, a light emitting device comprises: a radiation source and an emitting portion in optical communication with the radiation source, wherein the emitting portion is formed from a plastic composition. The plastic composition comprises the polycarbonate formed by any of the processes disclosed above and a conversion material, the conversion material is optionally coated. The conversion material comprises greater than 0 ppm of a first material selected from Si, Sr, Ba, Ca, Eu, and combinations comprising at least one of the foregoing first materials; and less than 50 ppm of a second material selected from Al, Co, Fe, Mg, Mo, Na, Ni, Pd, P, Rh, Sb, Ti, Zr, and combinations comprising at least one of the foregoing second materials. After the conversion material has been exposed to an excitation source, the conversion material has a luminescence lifetime of less than $10^{-4}$ seconds when the excitation source is removed.

In another embodiment, a lighting device comprises: a radiation source configured to emit radiation having a first wavelength range and an optical component comprising a plastic composition. The plastic composition comprises the polycarbonate formed by any of the processes disclosed above and a conversion material, the conversion material is optionally coated. The conversion material comprises greater than 0 ppm of a first material selected from Si, Sr, Ba, Ca, Eu, and combinations comprising at least one of the foregoing first materials; and less than 50 ppm of a second material selected from Al, Co, Fe, Mg, Mo, Na, Ni, Pd, P, Rh, Sb, Ti, Zr, and combinations comprising at least one of the foregoing second materials. After the conversion material has been exposed to an excitation source, the conversion material has a luminescence lifetime of less than $10^{-4}$ seconds when the excitation source is removed. The conversion material is configured to absorb at least a portion of the first wavelength range radiation and emit radiation having a second wavelength range; wherein the optical component is configured such that at least the first wavelength range radiation passes though the optical component.

In another embodiment, a light-emitting device comprises: a means for emitting radiation having a first wavelength range, wherein the means for emitting radiation is located in a housing formed from a plastic composition. The plastic composition comprises: the polycarbonate formed by any of the processes disclosed above, and means for absorbing at least a portion of the first wavelength range radiation and emitting radiation having a second wavelength range. After the means for absorbing has been exposed to the radiation, the means for absorbing has a luminescence lifetime of less than $10^{-4}$ seconds when the radiation exposure stops. The means for absorbing comprises greater than 0 ppm of a first material selected from Si, Sr, Ba, Ca, Eu, and combinations comprising at least one of the foregoing first materials; and less than 50 ppm of a second material selected from Al, Co, Fe, Mg, Mo, Na, Ni, Pd, P, Rh, Sb, Ti, Zr, and combinations comprising at least one of the foregoing second materials.

In another embodiment, a light emitting device comprises: a lighting element located in a housing. The housing is formed from a plastic composition comprising: the polycarbonate formed by any of the processes disclosed above and a conversion material. The conversion material can comprise yttrium aluminum garnet (YAG) doped with a rare earth element, terbium aluminum garnet doped with a rare earth element, silicate (BOSE) doped with a rare earth element; nitrido silicates doped with a rare earth element; nitride orthosilicate doped with a rare earth element, oxonitridoaluminosilicates doped with a rare earth element, and combinations comprising at least one of the foregoing. After the conversion material has been exposed to an excitation source, the conversion material has a luminescence lifetime of less than $10^{-4}$ seconds when the excitation source is removed.

Another embodiment is a plastic molded device formed from a plastic composition comprising the polycarbonate formed by any of the processes disclosed above and a conversion material, wherein the conversion material comprises yttrium aluminum garnet (YAG) doped with a rare earth element, terbium aluminum garnet doped with a rare earth element, silicate (BOSE) doped with a rare earth element; nitrido silicates doped with a rare earth element; nitride orthosilicate doped with a rare earth element, oxonitridoaluminosilicates doped with a rare earth element, and combinations comprising at least one of the foregoing. After the conversion material has been exposed to an excitation source, the conversion material has a luminescence lifetime of less than $10^{-4}$ seconds when the excitation source is removed.

Another embodiment is a light emitting device comprising: a radiation source; and an emitting portion in optical communication with the radiation source. The emitting portion is formed from a plastic composition, wherein the plastic composition comprises: the polycarbonate formed by any of the processes disclosed above, and a conversion material. The conversion material comprises yttrium aluminum garnet (YAG) doped with a rare earth element, terbium aluminum garnet doped with a rare earth element, silicate (BOSE) doped with a rare earth element; nitrido silicates doped with a rare earth element; nitride orthosilicate doped with a rare earth element, oxonitridoaluminosilicates doped with a rare earth element, and combinations comprising at least one of the foregoing. After the conversion material has been exposed to an excitation source, the conversion material has a luminescence lifetime of less than $10^{-4}$ seconds when the excitation source is removed.

In yet another embodiment, a lighting device comprises: a radiation source configured to emit radiation having a first wavelength range and an optical component comprising a plastic composition. The plastic composition comprises: the polycarbonate formed by any of the processes disclosed above and a conversion material. The conversion material comprises yttrium aluminum garnet (YAG) doped with a rare earth element, terbium aluminum garnet doped with a rare earth element, silicate (BOSE) doped with a rare earth element; nitrido silicates doped with a rare earth element; nitride orthosilicate doped with a rare earth element, oxonitridoaluminosilicates doped with a rare earth element, and combinations comprising at least one of the foregoing. The conversion material is configured to absorb at least a portion of the first wavelength range radiation and emit radiation having a second wavelength range. The optical component is configured such that at least the first wavelength range radiation passes though the optical component. After the conversion material has been exposed to an excitation source, the conversion material has a luminescence lifetime of less than $10^{-4}$ seconds when the excitation source is removed.

In still another embodiment, a light-emitting device comprises: a means for emitting radiation having a first wavelength range, wherein the means for emitting radiation is located in a housing. The housing is formed from a plastic composition comprising: a polycarbonate formed from any of the processes disclosed above; and means for absorbing at least a portion of the first wavelength range radiation and emitting radiation having a second wavelength range. After the means for absorbing has been exposed to the radiation, the means for absorbing has a luminescence lifetime of less than $10^{-4}$ seconds when the radiation exposure stops. The means for absorbing comprises greater than 0 ppm of a first material selected from at least one of the following Si, Sr, Ba, Ca, Eu, and combinations comprising at least one of the foregoing first materials; and less than 50 ppm of a second material selected from at least one of the following Al, Co, Fe, Mg, Mo, Na, Ni, Pd, P, Rh, Sb, Ti, Zr, and combinations comprising at least one of the foregoing second materials.

In the various embodiments, (i) the molded device, housing, optical component, and/or emitting portion, has a transparency of greater than or equal to 30% measured according to ASTM D1003-00, Procedure B, illuminant C, on a spectrophotometer, at a thickness of 1.04 mm; and/or (ii) the plastic composition further comprises a light diffusing material selected from crosslinked polymethylmethacrylate (PMMA), polytetrafluoroethylene, and methylsesquioxane, and combinations comprising at least one of the foregoing.

The following non-limiting examples further illustrate embodiments disclosed herein.

EXAMPLES

Example 1

As can be seen from the data set forth in Table 1 below, the sulfur level in a BPA sample having a BPA organic purity of 99.598 weight percent can be reduced from 23 ppm sulfur based upon the total weight of BPA down to 8 ppm with the addition of a strong base, potassium hydroxide (KOH). As shown in Table 1, the purity level decreased by only 0.367, while the sulfur decreased by 15 ppm. Table 1 further shows that when an anion exchange resin (AEX) was added instead of the KOH, even further improvements in purity and reduction in sulfur level resulted. In particular, treating the BPA having an initial ppBPA organic purity of 99.598 weight percent with the resin bound base (anion exchange resin, AEX) resulted in a ppBPA purity of 99.526 weight percent, which is a reduction in purity of only 0.072, and a sulfur reduction from 23 ppm down to 3 ppm based on BPA, which is a 20 ppm reduction in sulfur.

The experimental conditions were carried out as follows. For each treatment, 0.5 grams of BPA flakes were dissolved in 5 milliliters (ml) of high performance liquid chromatography (HPLC) grade methanol in a 25 ml glass sample preparation vial. A heating block was used for temperature control.

The following treatments were applied: Sample 1 was capped and heated at 80° C. for 6 hours. To Sample 2, 1 ml of 10% mass/volume (w/v) potassium hydroxide (KOH) in methanol was added before capping and heating at 80° C. for 6 hours. To Sample 3, 2 grams (g) of Rohm & Haas AMBERLYST* A-21 anion exchange beads ("A-21 resin") were added before capping and heating at 80° C. for 6 hours. After the heating, the samples were allowed to cool before filtering (0.45 micrometers (μm)) into a fresh sample prep vial. Next, 10 ml of methanol was used to wash the used vial and beads left in the filtration syringe. The washings were then collected. All samples were then evaporated at 80° C. for 5 hours under a stream of nitrogen.

TABLE 1

|  |  | BPA Sample 1 | BPA KOH Sample 2 | BPA AEX Sample 3 |
|---|---|---|---|---|
| ppBPA | (% wt.) | 99.598 | 99.231 | 99.526 |
| SULFUR | (ppm) | 23 | 8 | 3 |

Example 2

Table 2, which is explained in further detail below, sets forth further data demonstrating the significant reduction in sulfur (S) achievable, according to embodiments.

TABLE 2

| sample | A-21 resin grams | BPA grams | PhOH grams | total grams | BPA % wt. | total S start ppm | total S after ppm | S removed % | temp ° C. | time hrs | water % | catalyst state |
|---|---|---|---|---|---|---|---|---|---|---|---|---|
| 4 | 2.077 | 4.069 | 6.010 | 10.079 | 40.4 | 7.9 | 3.1 | 61 | 86 | 1 | 0 | wet |
| 5 | 2.008 | 4.122 | 6.070 | 10.192 | 40.4 | 7.9 | 2.8 | 65 | 86 | 2 | 0 | wet |
| 6 | 2.016 | 4.065 | 6.020 | 10.085 | 40.3 | 7.9 | 3.0 | 62 | 86 | 3 | 0 | wet |
| 7 | 1.516 | 4.006 | 6.060 | 10.066 | 39.8 | 7.8 | 3.3 | 58 | 86 | 2 | 0 | wet |
| 8 | 1.052 | 4.102 | 6.010 | 10.112 | 40.6 | 8.0 | 3.7 | 53 | 86 | 1 | 0 | wet |
| 9 | 1.023 | 4.228 | 6.030 | 10.258 | 41.2 | 8.1 | 3.1 | 62 | 86 | 3 | 0 | wet |
| 10 | None | 4.020 | 6 | 10.020 | 40.1 | 7.9 | 8.1 | −3 | 86 | 2 | 0 | — |
| 11 | None | 4.005 | 6 | 10.005 | 40.0 | 7.8 | 8.0 | −2 | 86 | 2 | 0 | — |
| 12 | None | 10 | — | 10 | 100.0 | 19.6 |  |  |  |  | 0 | — |
| 13 | 0.11 | 5.51 | 4.54 | 10.05 | 54.8 | 12.6 | 3.0 | 76 | 100 | 6 | 0 | dry |
| 14 | 0.06 | 5.52 | 4.51 | 10.03 | 55.1 | 12.7 | 8.7 | 31 | 100 | 6 | 0 | dry |
| 15 | 0.06 | 5.53 | 4.56 | 10.09 | 54.8 | 12.6 | 6.7 | 47 | 100 | 6 | 0 | dry |
| 16 | 0.21 | 5.54 | 4.50 | 10.04 | 55.1 | 12.7 | 8.1 | 36 | 100 | 6 | 0 | dry |
| 17 | 0.10 | 5.50 | 4.55 | 10.05 | 54.7 | 12.6 | 8.9 | 29 | 100 | 6 | 0 | dry |
| 18 |  | 10 |  | 10 | 100.0 | 23 |  |  |  |  |  |  |
| 19 | 0.06 | 4.00 | 4.70 | 8.70 | 46.0 | 10.5 | 4.4 | 58 | 100 | 6 | 10 | dry |
| 20 | 0.06 | 4.20 | 4.10 | 8.30 | 50.6 | 11.6 | 4.1 | 65 | 100 | 6 | 10 | dry |
| 21 | 0.10 | 3.90 | 3.80 | 7.70 | 50.6 | 11.6 | 3.9 | 66 | 100 | 6 | 10 | dry |
| 22 | 0.10 | 4.60 | 5.20 | 9.80 | 46.9 | 10.7 | 4.9 | 54 | 100 | 6 | 10 | dry |
| 23 | 0.21 | 4.00 | 3.60 | 7.60 | 52.6 | 12.0 | 3.8 | 68 | 100 | 6 | 10 | dry |
| 24 | 0.21 | 3.40 | 3.40 | 6.80 | 50.0 | 11.4 | 3.4 | 70 | 100 | 6 | 10 | dry |

TABLE 2-continued

| sample | A-21 resin grams | BPA grams | PhOH grams | total grams | BPA % wt. | total S start ppm | total S after ppm | S removed % | temp ° C. | time hrs | water % | catalyst state |
|---|---|---|---|---|---|---|---|---|---|---|---|---|
| 25 | 0.21 | 5.00 | 5.40 | 10.40 | 48.1 | 11.0 | 5.2 | 53 | 100 | 6 | 10 | dry |
| 26 |  | 10.20 | 11.40 | 21.60 | 47.2 | 10.8 | 10.8 | 0 | 100 | 6 | 10 | — |

Samples 4 to 11 used the same BPA source as that of the BPA Sample 12, which included 19.6 ppm total sulfur, as indicated in Table 2. The starting sulfur content was calculated for each sample from the mixture composition of BPA and phenol, and the 19.6 ppm sulfur that had been determined in the BPA source. The PhOH was sulfur free.

Similarly, Samples 13 to 17 used the same BPA source as that of the BPA Sample 18, which included 23 ppm total sulfur, as indicated in Table 2. The starting sulfur content also was calculated from the mixture composition of BPA and phenol, and the 23 ppm sulfur that had been determined in the BPA source. The PhOH also was sulfur free in these samples.

Samples 19 to 26 used the same BPA source as each other. A sample of the mixture of Sample 26 was analyzed for sulfur. The 10.8 ppm sulfur content of this mixture (Sample 26) was used to calculate starting values for the sulfur content for Samples 19 to 25, which were made from the same BPA, as well as PhOH source.

It is noted that the total sulfur amounts after treatment were determined experimentally, as further described below.

The following procedure of the sulfur removal experiments in the presence of ion exchange resin, A-21, was applied. Before using the A-21 resin for the sulfur removal experiments, the material was thoroughly washed with demineralized water. A conductivity measurement was conducted on the effluent after each treatment and the resin was released when the conductivity measured less than or equal to 20 microsiemens per centimeter (μS/cm).

As it could be difficult to control the moisture content (70 to 90 wt %) in the wet A-21 resin, part of the material was also dried and used in separate tests with water addition. The amount of water typically added was 10 wt % based upon the total weight of BPA and phenol.

Sample Preparation and Test Conditions

In a 25 ml glass vial, the A-21 resin was added first, followed by BPA and phenol. In the first series, wet A-21 resin was used for the sulfur removal. After preparation of the mixture of A-21 resin, BPA and phenol, the 25 ml vial was closed and exposed to 86° C. in a preheated oven for 1, 2, or 3 hours.

In the second series, dried A-21 resin was used for the sulfur removal. After preparation of the mixture of A-21 resin, BPA, and phenol, water was then added before the 25 ml vial was closed and exposed to 100° C. in a preheated oven for 6 hours.

The different exposure conditions for wet and dried resins were applied because the different water concentrations resulted in different behavior to completely melt the mixture of BPA and phenol.

The Total Sulfur Measurement

The total sulfur measurement was based on the destruction of a 40 milligram (mg) sample at 1100° C. The vapors emanating from the sample during the destruction were led through a scrubber followed by a fluorescence detector with a flow of argon and oxygen. Under these conditions, the sulfur was converted into sulfur dioxide ($SO_2$). The total sulfur concentration in the original 40 mg sample was determined based on the response of the fluorescence detector.

The BPA organic purity can be defined as 100 wt % minus the sum of known and unknown impurities detected using ultraviolet (UV) (see HPLC method in Nowakowska et al., Polish J. Appl. Chem., XI(3), 247-254 (1996)).

As can be seen from the data set forth in Table 2, specifically regarding Samples 4 to 9, when a mixture of BPA and PhOH is molten and treated with the basic ion exchange resin, a significant amount of the sulfur is removed. However, in the absence of the resin and under otherwise the same experimental conditions, the same heat treatment does not result in a reduction of the sulfur level (see Samples 10 and 11 where no resin was employed and no reduction in sulfur resulted). In these experiments the catalyst was undried and contained some humidity.

Samples 13 to 17 show that also at much lower levels of basic ion exchange resins and higher levels of BPA, sulfur can be effectively removed in significant amounts. In these experiments, the ion exchange resin had been dried before use. The BPA content of these samples was in a practical range that also can be encountered in the plant stream at reference 54 (FIGS. 2-4): 45 to 70 wt %, for example.

Samples 19 to 25 repeat these experiments, but now in the presence of 10 wt % water. Also in these cases, a significant amount of sulfur was removed, as shown in Table 2.

Examples 1-2 demonstrate that the addition of a base is effective in significantly reducing the amount of sulfur present in BPA, and thus is effective in enabling the production of high quality BPA, as well as high quality polycarbonate made from the resultant BPA. Such products also can be characterized by a reduction or elimination of noxious smell and enhanced color due to the low levels of sulfur achievable, according to embodiments.

In general, the embodiments may alternately comprise, consist of, or consist essentially of, any appropriate components herein disclosed. The embodiments may additionally, or alternatively, be formulated so as to be devoid, or substantially free, of any components, materials, ingredients, adjuvants or species used in prior art compositions or that are otherwise not necessary to the achievement of the function and/or objectives of the embodiments herein.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, terms "first," "second,", "initial", and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

As used herein, the term "conversion material" refers to an inorganic material that converts radiation of a certain wavelength and re-emits of a different wavelength (much lower energy). A conversion material that causes luminescence and/or scintillation (which is characterized by energy loss of ionizing radiation through matter) may exist, for example, in the powder form or as a transparent single crystal. The conversion material converts some of the blue light from a blue LED to yellow light and the overall combination of available light is perceived as white light to an observer. The lifetime of yellow light produced in this manner (or other colors from conversion material(s)) is very short, lasting less than $10^{-4}$ seconds (i.e., lifetime when the excitation source is removed). Lifetimes of this order may be regarded as fluorescence lifetimes (lasting less than $10^{-4}$ seconds, e.g, lasting $10^{-4}$ to $10^{-9}$ seconds). A conversion material does not produce a long afterglow (lifetime duration generally lasting minutes and even hours). When the excitation source is removed, luminescence ceases (i.e., no long after-glow).

The notation $(C_n-C_m)$ and the notation $(C_{n-m})$ means a group containing from n to m carbon atoms per group.

"Melt-Volumetric Rate" (MVR) of a molten polymer is measured by determining the amount of polymer that flows through a capillary of a specific temperature over a specified time using standard weights at a fixed temperature. MVR is expressed in cubic centimeter per 10 minutes (cc/10 min). The higher the MVR value of a polymer at a specific temperature, the greater the flow of that polymer at that specific temperature. As used herein, MVR is determine in accordance with ASTM D1238-10 at a temperature of 300° C., after extrusion into a pellet, with a weight of 1.2 kilogram (kg).

The pKa values used in the model for the end-capping agents are listed in Table 3 below:

TABLE 3

| End-capping agent | pKa* |
|---|---|
| p-cyanophenol | 8.2 |
| p-methyl-hydroxy benzoate | 8.4 |
| phenol | 9.9 |
| p-t-butylphenol | 10.2 |
| p-methoxyphenol | 10.4 |
| p-cumylphenol | 10.5 |

*pKa values for all of the end-capping agents but p-t-butyl phenol and p-cumylphenol were obtained from the following reference: J.AM. CHEM. SOC. 2002, 6424. The values chosen in the reference were listed in the S7 category in Table 3 of the reference. The pKa value for p-t-butylphenol was obtained from the following reference: Journal of Molecular Structure: THEOCHEM 805, 2006, 31. The pKa for methyl-p-hydroxybenzoate was obtained from the following reference: Chromatographia Vol. 39, No. 5/6, September 1994. The pKa value for p-cumylphenol was approximated based on the values of similar structures.

"Transparency" as used herein refers to that percentage of transmitted light, which in passing through a specimen deviates from the incident beam by forward scattering. Percent (%) transparency can be measured according to ASTM D1003-00, Procedure B, illuminant C, on a spectrophotometer.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A light emitting device, comprising:
   a lighting element located in a housing, wherein the housing is formed from a plastic composition comprising:
   a polycarbonate formed from reacting, in the presence of a transesterification catalyst, a diaryl carbonate ester and a bisphenol A, wherein the bisphenol A has a sulfur concentration of 1 ppm to 15 ppm, based upon a weight of the bisphenol A; and
   a conversion material wherein the conversion material comprises an inorganic material that converts radiation of a certain wavelength and re-emits of a different wavelength;
   wherein after the conversion material has been exposed to an excitation source, the conversion material has a luminescence lifetime of less than $10^{-4}$ seconds when the excitation source is removed.

2. The device of claim 1, wherein the lighting element is a radiation source, and wherein the housing is an emitting portion that is in optical communication with the radiation source.

3. The device of claim 2,
   wherein the radiation source is configured to emit radiation having a first wavelength range;
   wherein the conversion material is configured to absorb at least a portion of the first wavelength range radiation and emit radiation having a second wavelength range;
   wherein the housing is configured such that at least the first wavelength range radiation passes though the housing; and
   wherein after the conversion material has been exposed to an excitation source, the conversion material has a luminescence lifetime of less than $10^{-4}$ seconds when the excitation source is removed.

4. The device of claim 1, wherein the plastic composition further comprises greater than 0 to 1 pbw particles, based upon 100 pbw of polycarbonate, wherein the particles are selected from at least one of the following scattering particles, interference particles, and color absorbing particles.

5. The device of claim 1, wherein the conversion material comprises a luminescent material having the formula:

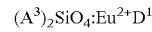

wherein $A^3$ is a divalent metal selected from at least one of the following Sr, Ca, Ba, Mg, Zn, Cd, and combinations comprising at least one of the foregoing; and $D^1$ is a dopant selected from at least one of the following F, Cl, Br, I, P, S and N and combinations comprising at least one of the foregoing.

6. The device of claim 1, wherein the conversion material comprises a luminescent material having formula:

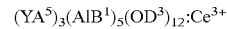

where $A^5$ is a trivalent metal selected from at least one of the following Gd, Tb, La, Sm, luminescence, or a divalent metal ion selected from Sr, Ca, Ba, Mg, Zn and Cd, and combinations comprising at least one of the foregoing; $B^1$ is selected from at least one of the following Si, B, P, and Ga, and combinations comprising at least one of the foregoing; and $D^3$ is a dopant selected from F, Cl, Br, I, P, S, and N, and combinations comprising at least one of the foregoing.

7. The device of claim 1, wherein the conversion material comprises an orange-red silicate-based conversion material having formula:

$$(SrM1)_3Si(OD^4)_5:Eu$$

wherein M1 is selected from at least one of the following Ba, Ca, Mg, Zn, and combinations comprising at least one of the foregoing; and $D^4$ is selected from F, Cl, S, N, and combinations comprising at least one of the foregoing.

8. The device of claim 1, wherein the conversion material comprises an $Eu^{2+}$ and/or $Dy^{3+}$ doped conversion material having formula:

$$M_3MgSi_2O_8$$

wherein M is selected from at least one of the following Ca, Sr, Ba, and combinations comprising at least one of the foregoing.

9. The device of claim 1, wherein the conversion material comprises a rare earth doped a red silicon nitride based conversion material having a formula:

$$(SrM2)_2Si_5N_8$$

wherein M2 is selected from at least one of the following Sr, Ca, Mg, Zn, and combinations comprising at least one of the foregoing.

10. The device of claim 1, wherein the conversion material comprises a rare earth doped a red sulfate based conversion material having formula:

$$(SrM3)S$$

wherein M3 is selected from at least one of the following Ca, Ba, Mg, and combinations comprising at least one of the foregoing.

11. The device of claim 1, wherein the conversion material is a green sulfate based conversion material having formula:

$$(SrM3)(GaM4)_2S_4:Eu$$

wherein M3 is selected from at least one of the following Ca, Ba, Mg, and combinations comprising at least one of the foregoing; and M4 is selected from at least one of the following Al and In, and combinations comprising at least one of the foregoing.

12. The device of claim 1, wherein the conversion material is selected from at least one of the following: a strontium silicate yellow conversion material; yttrium aluminum garnet doped with rare earth element; terbium aluminum garnet doped with a rare earth element; silicate conversion materials; nitride conversion materials; nitrido silicates; nitride orthosilicate; oxonitridoaluminosilicates; and combinations comprising at least one of the foregoing.

13. The device of claim 1, wherein the conversion material is a selected from at least one of the following: combinations of yellow conversion material with a red conversion material; combinations of green and red conversion material; a semiconductor nanocrystals of cadmium sulfide mixed with manganese; and combinations comprising at least one of the foregoing.

14. The device of claim 1, wherein the conversion material comprises a silicone oil coating.

15. The device of claim 14, wherein the conversion material is coated with 0.05 wt % to 20 wt % silicone oil based upon the weight of the conversion material and silicone oil.

16. The device of claim 14, wherein the silicone oil is selected from at least one of the following hydrogen-alkyl siloxane oil; polydialkyl siloxane oil; polydimethyl siloxane codiphenyl siloxane, dihydroxy terminated, and combinations comprising at least one of the foregoing.

17. The device of claim 1, wherein the conversion material comprises an amorphous silica coating.

18. The device according to claim 1, wherein the device is at least one of the following: a lamp, illumination device, lighting device for applications in the interior and exterior area, vehicle lighting, internal lighting of residential and work rooms, backlight units of LCD screens, and accent lighting.

19. The device according to claim 1, wherein the device is a backlight unit of a LCD screen.

20. A plastic molded device having a transparency of greater than or equal to 30% measured according to ASTM D1003-00, Procedure B, illuminant C, on a spectrophotometer, and at a thickness of 1.04 mm, wherein the article is formed from the plastic composition comprising:
  a polycarbonate formed from reacting, in the presence of a transesterification catalyst, a diaryl carbonate ester and a bisphenol A, wherein the bisphenol A has a sulfur concentration of 1 ppm to 15 ppm, based upon a weight of the bisphenol A; and
  a conversion material wherein the conversion material comprises an inorganic material that converts radiation of a certain wavelength and re-emits of a different wavelength;
wherein after the conversion material has been exposed to an excitation source, the conversion material has a luminescence lifetime of less than $10^{-4}$ seconds when the excitation source is removed.

* * * * *